US011084862B2

(12) United States Patent
Molloy et al.

(10) Patent No.: US 11,084,862 B2
(45) Date of Patent: Aug. 10, 2021

(54) T CELL RECEPTORS

(71) Applicant: Adaptimmune Limited, Abingdon (GB)

(72) Inventors: Peter Molloy, Abingdon (GB); Nicholas Pumphrey, Abingdon (GB)

(73) Assignee: ADAPTIMMUNE LIMITED, Abingdon (GB)

( * ) Notice: Subject to any disclaimer, the term of this patent is extended or adjusted under 35 U.S.C. 154(b) by 0 days.

(21) Appl. No.: 16/416,907

(22) Filed: May 20, 2019

(65) Prior Publication Data
US 2019/0330301 A1 Oct. 31, 2019

Related U.S. Application Data

(60) Division of application No. 15/006,224, filed on Jan. 26, 2016, now Pat. No. 10,344,074, which is a continuation-in-part of application No. PCT/GB2014/052199, filed on Jul. 18, 2014.

(30) Foreign Application Priority Data

Jul. 26, 2013 (GB) .................................. 1313377.2

(51) Int. Cl.
C07K 14/725 (2006.01)
C12N 5/0783 (2010.01)
A61K 39/00 (2006.01)
A61K 38/00 (2006.01)

(52) U.S. Cl.
CPC ...... *C07K 14/7051* (2013.01); *A61K 39/0011* (2013.01); *A61K 39/001181* (2018.08); *C12N 5/0637* (2013.01); *A61K 38/00* (2013.01); *C12N 2740/15043* (2013.01); *C12N 2799/027* (2013.01)

(58) Field of Classification Search
None
See application file for complete search history.

(56) References Cited

U.S. PATENT DOCUMENTS 7,329,731 B2 2/2008 Jakobsen

FOREIGN PATENT DOCUMENTS

| JP | 2008-263950 | 11/2008 |
| WO | 03/020763 | 3/2003 |
| WO | 2004/033685 | 4/2004 |
| WO | 2006/000830 | 1/2006 |
| WO | 2007131092 A2 | 1/2007 |
| WO | 2008/038002 | 4/2008 |

OTHER PUBLICATIONS

Sasaki et al., Cancer Letters 308 (2011) 152-161. (Year: 2011).*
Popovic et al. (Blood. 2011; 118(4):946-954). (Year: 2011).*
Bossi et al. (Oncolmmunology, 2013, 2:11, e26840). (Year: 2013).*
Nakatsugawa et al., International Journal of Oncology 39: 1041-1049, 2011. (Year: 2011).*
Stanislawski et al., Nat Immunol. (Oct. 2001) 2(10):962-70.
Zhao et al., J Immunol. (2005) 174:4415-4423.
Janeway et al., Immunobiology, 5th Ed., Garland Science (2001) pp. 106-108 and 260-263.
Garcia et al., Cell (Aug. 12, 2005) vol. 122, p. 333-336.
Goyarts et al., Mol Immunol. (Jul. 1998) 35(10):593-607.
Robins et al., Blood (2009) 114:4099-4107.
Marodon et al., Eur. J. Immunol. (2009) 39:2136-2145.
Portolano et al., J Immunol. (Feb. 1. 1993):150(3):880-7.
Butterfield, et al., A Phase I/II Trial Testing Immunization of Hepatocellular Carcinoma Patients with Dendritic Cells Pulsed with Four α-Fetoprotein Peptides, Clinical Cancer Research (May 2006) 12(9):2817-2825.
Butterfield, et al., Generation of Human T-cell Response to an HLA-A2.1-restricted Peptide Epitope Derived from α-Fetoprotein, Cancer Research (Jul. 1999) 59:3134-3142.
Butterfield, et al., T Cell Responses to HLA-A *0201-Restricted Peptides Derived from Human α-Fetoprotein, The Journal of Immunology (Apr. 2001) 166(8):5300-5308.
Gerry, et al., Improved Affinity AFP-specific T Cell Receptor for Hepatocellular Carcinoma, Journal for Immuno Therapy of Cancer (Nov. 2013) 1 (Suppl 1):P10.
Kuball, et al., Increasing functional avidity of TCR-redirected T cells by removing defined N-glycosylation sites in the TCR constant domain, Journal of Experimental Medicine (Jan. 2009) 206(2):463-475.
Li, et al., Directed evolution of human T-cell receptors with picomolar affinities by phage display: Nature Biotechnology (Feb. 2005) 23(3):349-354.
O'Callaghan, et al. BirA enzyme: production and application in the study of membrane receptor-ligand interactions by site-specific biotinylation, Anal. Biochem. (Jan. 1999) 266(1):9-15.
Pichard, et al., Detection, Isolation, and Characterization of α-fetoprotein-specific T Cell Populations and Clones Using MHC Class I Multimer Magnetic Sorting, Journal of Immunotherapy (Apr. 2008) 31(3):246-253.
Price & Dwek, Principles and Problems in Physical Chemistry for Biochemists (2nd Edition) 1979, Clarendon Press, Oxford.
Rashtchian, Novel methods for cloning and engineering genes using the polymerase chain reaction, Curr. Opin. Biotechnol (Feb. 1995) 6(1):30-36.
Robbins, et al., Single and dual amino acid substitutions in TCR CDRs can enhance antigen-specitic T cell functions, Journal of Immunology (May 2008) 180(9):6116-6131.

(Continued)

*Primary Examiner* — Zachary S Skelding
(74) *Attorney, Agent, or Firm* — Duane Morris LLP; Thomas J. Kowalski; Deborah L. Lu

(57) ABSTRACT

The present invention relates to T cell receptors (TCRs) which bind the HLA-A2 restricted FMNKFIYEI (158-166) peptide epitope derived from α Fetoprotein (AFP). Certain preferred TCRs of the invention demonstrate excellent binding characteristics and specificity profiles for this AFP epitope. T cell receptors of the invention may comprise at least one TCR alpha chain variable domain and/or at least one TCR beta chain variable domain, the alpha chain variable domain which may comprise an amino acid sequence that has at least 90% identity to the sequence of amino acid residues 1-112 of SEQ ID No: 2, and/or the beta chain variable domain which may comprise an amino acid sequence that has at least 90% identity to the sequence of amino acid residues 1-112 of SEQ ID No: 3.

6 Claims, 11 Drawing Sheets

Specification includes a Sequence Listing.

(56) References Cited

OTHER PUBLICATIONS

Rosenberg, et al., Adoptive cell transfer: a clinical path to effective cancer immnotherapy, Nat Rev. Cancer (Apr. 2008) 8(4):299-308.
Sambrook & Russell, (2001) Molecular Cloning—A Laboratory Manual (3rd Ed.) CSHL Press.
T Cell Receptor Factsbook, (2001) LeFranc and LeFranc, Academic Press ISBN 0-12-441352-8.
Zhao, et al., High-affinity TCRs generated by phage display provide CD4+ T cells with the ability to recognize and kill tumor cell lines, Journal of Immunology (Nov. 2007) 179(9):5845-5854.
International Search Report and Written Opinion dated Oct. 30, 2014, issued in International Application No. PCT/GB2014/052199.

* cited by examiner

Figure 1

**Parental AFP TCR TRAV12-2*02/TRAJ41*01/TRAC alpha chain amino acid extracellular sequence (SEQ ID No: 2)**

Parental AFP TCR TRBV9*01/TRBD2/TRBJ2-7*01/TRBC2 beta chain amino acid extracellular sequence (SEQ ID No: 3)

Reference TCR alpha chain – parental AFP-specific TCR alpha chain extracellular amino acid sequence, with cysteine (bold and underlined) substituted for T159 (i.e. T48 of TRAC) (SEQ ID No: 4)

Reference TCR beta chain – Parental AFP-specific TCR beta chain extracellular amino acid sequence, with cysteine (bold and underlined) substituted for S168 (i.e. S57 of TRBC2) and with A187 substituted for C187 and D201 substituted for N201 (SEQ ID No: 5)

Alpha chain amino acid sequence (SEQ ID Nos: 6-20)

ADB 327 (SEQ ID No: 6)
QKEVEQNSGPLSVPEGAIASLNCTYSDRGSQAFFWYRQYSGKSPELIMSIYSNGDKEDGRFTAQL
NKASQYVSLLIRDSQPSDSATYLCAVNSDSGYALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 329 (SEQ ID No: 7)
QKEVEQNSGPLSVPEGAIASLNCTYSDRGSQSFFWYRQYSGKSPELIMSIYSNGDKEDGRFTAQL
NKASQYVSLLIRDSQPSDSATYLCAVNSDSSYALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 330 (SEQ ID No: 8)
QKEVEQNSGPLSVPEGAIASLNCTYSDRGSQSFFWYRQYSGKSPELIMSIYSNGDKEDGRFTAQL
NKASQYVSLLIRDSQPSDSATYLCAVNSDSGVALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 331 (SEQ ID No: 9)
QKEVEQNSGPLSVPEGAIASLNCTYSDRGSQAFFWYRQYSGKSPELIMSIYSNGDKEDGRFTAQL
NKASQYVSLLIRDSQPSDSATYLCAVNSDSGVALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 328 (SEQ ID No: 10)
QKEVEQNSGPLSVPEGAIASLNCTYSDRGSQSFFWYRQYSGKSPELIMSIYSNGDKEDGRFTAQL
NKASQYVSLLIRDSQPSDSATYLCAVNSQSGYALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 352 (SEQ ID No: 11)
QKEVEQNSGPLSVPEGAIASLNCTYSDRGSQSFFWYRQYSGKSPELIMSIYSNGDKEDGRFTAQL
NKASQYVSLLIRDSQPSDSATYLCAVNSQSGYSLNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 350 (SEQ ID No: 12)
QKEVEQNSGPLSVPEGAIASLNCTYSDRGSQSFFWYRQYSGKSPELIMSIYSNGDKEDGRFTAQL
NKASQYVSLLIRDSQPSDSATYLCAVNSQSSYALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 332 (SEQ ID No: 13)
QKEVEQNSGPLSVPEGAIASLNCTYSDRGSQAFFWYRQYSGKSPELIMSIYSNGDKEDGRFTAQL
NKASQYVSLLIRDSQPSDSATYLCAVNSQSGYALNFGKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

Figure 5 continued

ADB 351 (SEQ ID No: 14)
QKEVEQNSGPLSVPEGAIASLNCTYS<u>DRGSQS</u>FFWYRQYSGKSPELIMS<u>IYSNGD</u>KEDGRFTAQL
NKASQYVSLLIRDSQPSDSATYLC<u>AVNSQSGVALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 349 (SEQ ID No: 15)
QKEVEQNSGPLSVPEGAIASLNCTYS<u>DRGSQS</u>FFWYRQYSGKSPELIMS<u>IYSNGD</u>KEDGRFTAQL
NKASQYVSLLIRDSQPSDSATYLC<u>AVNSQNGYALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 353 (SEQ ID No: 16)
QKEVEQNSGPLSVPEGAIASLNCTYS<u>DRGSFS</u>FFWYRQYSGKSPELIMS<u>IYSNGD</u>KEDGRFTAQL
NKASQYVSLLIRDSQPSDSATYLC<u>AVNSDSGYALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 326 (SEQ ID No: 17)
QKEVEQNSGPLSVPEGAIASLNCTYS<u>DRGSIS</u>FFWYRQYSGKSPELIMS<u>IYSNGD</u>KEDGRFTAQL
NKASQYVSLLIRDSQPSDSATYLC<u>AVNSDSGYALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 333 (SEQ ID No: 18)
QKEVEQNSGPLSVPEGAIASLNCTYS<u>DRGSIS</u>FFWYRQYSGKSPELIMS<u>IYSNGD</u>KEDGRFTAQL
NKASQYVSLLIRDSQPSDSATYLC<u>AVNSDSSYALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 334 (SEQ ID No: 19)
QKEVEQNSGPLSVPEGAIASLNCTYS<u>DRGSYS</u>FFWYRQYSGKSPELIMS<u>IYSNGD</u>KEDGRFTAQL
NKASQYVSLLIRDSQPSDSATYLC<u>AVNSDSGVALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

ADB 335 (SEQ ID No: 20)
QKEVEQNSGPLSVPEGAIASLNCTYS<u>DRGSYS</u>FFWYRQYSGKSPELIMS<u>IYSNGD</u>KEDGRFTAQL
NKASQYVSLLIRDSQPSDSATYLC<u>AVNSQSGYALNF</u>GKGTSLLVTPHIQNPDPAVYQLRDSKSSDK
SVCLFTDFDSQTNVSQSKDSDVYITDKTVLDMRSMDFKSNSAVAWSNKSDFACANAFNNSIIPEDT
FFPSPESS

Figure 6

Reference TCR alpha chain DNA sequence (SEQ ID No: 21)

caaaaagaagttgagcagaattctggaccccteagtgttccagagggagccattgcctctctcaactgcactt
acagtgaccgaggttcccagtccttcttctggtacagacaatattctgggaaaagccctgagttgataatgtc
catatactccaatggtgacaaagaagatggaaggtttacagcacagctcaataaagccagccagtatgtttct
ctgctcatcagagactccagcccagtgattcagccacctacctctgtgccgtgaatagtgattccgggtatg
cactcaacttcggcaaaggcacctcgctgttggtcacacccatatccagaaccctgaccctgccgtgtacca
gctgagagactctaagtcgagtgacaagtctgtctgctattcaccgatttgattctcaaacaaatgtgtca
caaagtaaggattctgatgtgtatatcacagacaaatgtgtgctagacatgaggtctatggacttcaagagca
acagtgctgtggcctggagcaacaaatctgactttgcatgtgcaaacgccttcaacaacagcattattccaga
agacaccttcttcccagcccagaaagttcc

Reference TCR beta chain DNA sequence (SEQ ID No: 22)

gattctggagtcacacaaaccccaaagcacctgatcacagcaactggacagcgagtgacgctgagatgctcc
ctaggtctggagaccttctctgtgtactggtaccaacagagcctggaccagggcctcagttcctcattcagta
ttataatggagaagagagagcaaaaggaaaacattcttgaacgattctccgcacaacagttccctgacttgcac
tctgaactaaacctgagctctctggagctgggggactcagctttgtatttctgtgccagcagcctcgggggg
aatctgagcagtacttcgggccgggcaccaggctcacggtcacagaggacctgaaaaacgtgttccaccga
ggtcgctgtgtttgagccatcagaagcagagatctcccacacccaaaaggccacactggtgtgcctggccac
cggttttctaccccgaccacgtggagctgagctggtgggtgaatgggaaggaggtgcacagtggggtctgcacag
acccgcagccccctcaaggagcagccgcctcaatgactccagatacgtctgagcagccgcctgagggtctc
ggccaccttctggcaggacccgcaaccacttccgtgtcaagtccagttctacgggctctcggagaatgac
gagtggaccaggatagggccaaacccgtcacccagatcgtcagcgccgaggctgggtagagcagac

Figure 7

Parental AFP TCR alpha chain-2A-beta chain DNA sequence with porcine teschovirus-1 2A sequence (bold and underlined) (SEQ ID No: 23) Restriction enzyme sites are underlined g<u>ctagc</u>cgccaccatgatgaagtccctgcggggtgctgctggtcatcctgtggctgcagctgtcctgggtctgg
tcccagcagaaagaggtggagcagaacagcggccctctgagcgtgcccgagggcgctatcgccagcctgaact
gcacctacagcgacagaggcagccagagcttcttctggtacagacagtacagcggcaagagccccgagctgat
catgagcatctacagcaacggcgacaaagaggacggccggttcaccgcccagctgaacaaggccagccagtac
gtgtccctgctgatccgggacagccagcccagcgacagcgccacctacctgtgcgccgtgaacagcgactccg
gctacgccctgaacttcggcaagggcacccagctgctggtgacacccacattcagaacccgacccgccgt
gtaccagctgcgggacagcaagagcagcgacaagagcgtgtgcctgttcaccgacttcgacagccagaccaac
gtgtcccagagcaaggacagcgacgtgtacatcaccgacaagaccgtgctggacatgcggagcatggacttca
agagcaacagcgccgtggcctggtccaacaagagcgacttcgcctgcgccaacgccttcaacaacagcatcat
ccccgaggacacattttttccaagcccgagagcagctgcgacgtcaaactggtggagaagtccttcgagaca
gacaccaacctgaacttccagaacctgagcgtgatcggcttcagaatcctgctgctgaaggtggccggcttca
tctgctgatgaccctgcggctgtggtccagcggcagcagagccaagagaagcggatccggc<b><u>gccaccaactt
cagcctgctgaagcaggccggcgacgtggaggaaaaccctggccct</u></b>aggatgggcttccggctgctgtgctgc
gtggccttctgctgctgggagccggccctgtggatagcggcgtgacccagacccccaagcacctgatcaccg
ccaccggcagagagtgaccctgcgctgcagccctagaagcggcgacctgtccgtgtactggtatcagcagag
cctggaccagggactgcagttcctcatccagtactacaacggcgaggaacgggccagggcaacatcctggaa
agattcagcgcccagcagttccccgacctgcacagcgagctgaacctgagcagcctggaactgggcgactccg
cctgtacttctgcgccagcagcctgggcggcgagagcgaacagtacttcggccctggcaccggctgacggt
aaccgaggacctgaagaacgtgttccccccagaggtggccgtgttcgagccctctgaggcgagatcagccac
aaccagaaagccacctggtctgcctggccacggcttctacccgaccacgtggaactgtcttggtgggtga
acggcaaagaggtgcacagcggcgtcagcacgaccctcagccctgaaagagcagccgccctgaacgacag
ccggtactgctgagcagcagactgcgggtgtccgccacttctggcagaaccccggaaccacttcagatgc
caggtcagttctacggcctgagcgagaacgacgagtggaccaggaccgggccaagcctgtgacccagatcg
tgtctgccgaagcatggggggcgcgccgattgcggcttcacaagcgagagctaccagcaggcgtgctgagcgc
cacattcctgtacgagatcctgctgggcaaggccaccctgtacgccgtgctggtgtccgctctggtgctgatg
gccatggtgaaacggaaggacagccggggctaataag<u>tcgac</u>

Figure 8

Parental AFP TCR alpha chain-2A-beta chain amino acid sequence with porcine teschovirus-1 2A sequence (bold and underlined) (SEQ ID No: 24)

Activation of AFP TCR engineered T cells (IFNγ production)

SEQUENCE LISTING

```
<160> NUMBER OF SEQ ID NOS: 28

<210> SEQ ID NO 1
<211> LENGTH: 9
<212> TYPE: PRT
<213> ORGANISM: Homo sapiens

<400> SEQUENCE: 1

Phe Met Asn Lys Phe Ile Tyr Glu Ile
1               5

<210> SEQ ID NO 2
<211> LENGTH: 205
<212> TYPE: PRT
<213> ORGANISM: Homo sapiens

<400> SEQUENCE: 2

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80
```

-continued

```
Pro Ser Asp Ser Ala Thr Tyr Leu Cys Ala Val Asn Ser Asp Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 3
<211> LENGTH: 242
<212> TYPE: PRT
<213> ORGANISM: Homo sapiens

<400> SEQUENCE: 3

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Leu Gly
                85                  90                  95

Gly Glu Ser Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp
```

<210> SEQ ID NO 4
<211> LENGTH: 205
<212> TYPE: PRT
<213> ORGANISM: Artificial sequence
<220> FEATURE:
<223> OTHER INFORMATION: T cell receptor alpha chain extracellular domain

<400> SEQUENCE: 4

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 5
<211> LENGTH: 242
<212> TYPE: PRT
<213> ORGANISM: Artificial sequence
<220> FEATURE:
<223> OTHER INFORMATION: T cell receptor beta chain extracellular domain

<400> SEQUENCE: 5

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Leu Gly
                85                  90                  95

Gly Glu Ser Glu Gln Tyr Phe Gly Pro Gly Thr Arg Leu Thr Val Thr

```
                    100                 105                 110
Glu Asp Leu Lys Asn Val Phe Pro Pro Glu Val Ala Val Phe Glu Pro
            115                 120                 125

Ser Glu Ala Glu Ile Ser His Thr Gln Lys Ala Thr Leu Val Cys Leu
130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
            195                 200                 205

Gln Val Gln Phe Tyr Gly Leu Ser Glu Asn Asp Glu Trp Thr Gln Asp
        210                 215                 220

Arg Ala Lys Pro Val Thr Gln Ile Val Ser Ala Glu Ala Trp Gly Arg
225                 230                 235                 240

Ala Asp
```

<210> SEQ ID NO 6
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 6

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ala
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
        130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205
```

<210> SEQ ID NO 7

```
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 7

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Ser
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 8
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 8

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Val Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
```

```
                 115                 120                 125

Ser Asp Lys Ser Val Cys Leu Phe Thr Asp Phe Asp Ser Gln Thr Asn
            130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
                195                 200             205

<210> SEQ ID NO 9
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 9

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ala
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Val Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
            130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
                195                 200             205

<210> SEQ ID NO 10
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 10

Gln Lys Glu Val Glu Gln Asn Ser Gly Pro Leu Ser Val Pro Glu Gly
1               5                   10                  15
```

```
Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 11
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 11

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Ser Gly
                85                  90                  95

Tyr Ser Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175
```

```
Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 12
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 12

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Ser Ser
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 13
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 13

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ala
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80
```

```
Pro Ser Asp Ser Ala Thr Tyr Leu Cys Ala Val Asn Ser Gln Ser Gly
            85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
            130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 14
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 14

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Ser Gly
            85                  90                  95

Val Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
            130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 15
<211> LENGTH: 205
<212> TYPE: PRT
<213> ORGANISM: Artificial sequence
```

<220> FEATURE:
<223> OTHER INFORMATION: T cell receptor alpha chain variable domain

<400> SEQUENCE: 15

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Asn Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 16
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 16

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Phe Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn

```
            130                 135                 140
Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 17
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 17

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Tyr Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Asp Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 18
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 18

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Tyr Ser
            20                  25                  30
```

```
Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
 50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Asn Ser Asp Ser Ser
                 85                  90                  95

Tyr Ala Leu Asn Phe Gly Lys Gly Thr Ser Leu Leu Val Thr Pro His
                100                 105                 110

Ile Gln Asn Pro Asp Pro Ala Val Tyr Gln Leu Arg Asp Ser Lys Ser
                115                 120                 125

Ser Asp Lys Ser Val Cys Leu Phe Thr Asp Phe Asp Ser Gln Thr Asn
130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
                180                 185                 190

Ile Pro Glu Asp Thr Phe Phe Pro Ser Pro Glu Ser Ser
                195                 200                 205

<210> SEQ ID NO 19
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 19

Gln Lys Glu Val Glu Gln Asn Ser Gly Pro Leu Ser Val Pro Glu Gly
 1               5                  10                  15

Ala Ile Ala Ser Leu Asn Cys Thr Tyr Ser Asp Arg Gly Ser Tyr Ser
                 20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
 50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Asn Ser Asp Ser Gly
                 85                  90                  95

Val Ala Leu Asn Phe Gly Lys Gly Thr Ser Leu Leu Val Thr Pro His
                100                 105                 110

Ile Gln Asn Pro Asp Pro Ala Val Tyr Gln Leu Arg Asp Ser Lys Ser
                115                 120                 125

Ser Asp Lys Ser Val Cys Leu Phe Thr Asp Phe Asp Ser Gln Thr Asn
130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
                180                 185                 190
```

```
Ile Pro Glu Asp Thr Phe Phe Pro Ser Pro Glu Ser Ser
        195                 200                 205
```

<210> SEQ ID NO 20
<211> LENGTH: 205
<212> TYPE: PRT
<213> ORGANISM: Artificial sequence
<220> FEATURE:
<223> OTHER INFORMATION: T cell receptor alpha chain variable domain

<400> SEQUENCE: 20

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Tyr Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ser Gln Ser Gly
                85                  90                  95

Tyr Ala Leu Asn Phe Gly Lys Gly Thr Ser Leu Leu Val Thr Pro His
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205
```

<210> SEQ ID NO 21
<211> LENGTH: 615
<212> TYPE: DNA
<213> ORGANISM: Artificial sequence
<220> FEATURE:
<223> OTHER INFORMATION: T cell receptor alpha chain extracellular
      domain

<400> SEQUENCE: 21

```
caaaaagaag ttgagcagaa ttctggaccc ctcagtgttc cagagggagc cattgcctct     60
ctcaactgca cttacagtga ccgaggttcc cagtccttct ctggtacag acaatattct    120 gggaaaagcc ctgagttgat aatgtccata tactccaatg gtgacaaaga gatggaagg    180 tttacagcac agctcaataa agccagccag tatgtttctc tgctcatcag agactcccag    240
cccagtgatt cagccaccta cctctgtgcc gtgaatagtg attccgggta tgcactcaac    300
ttcggcaaag gcacctcgct gttggtcaca ccccatatcc agaaccctga ccctgccgtg    360
taccagctga gagactctaa gtcgagtgac aagtctgtct gcctattcac cgatttgat    420 tctcaaacaa atgtgtcaca agtaaggat tctgatgtgt atatcacaga caaatgtgtg    480
```

| ctagacatga ggtctatgga cttcaagagc aacagtgctg tggcctggag caacaaatct | 540 |
| gactttgcat gtgcaaacgc cttcaacaac agcattattc cagaagacac cttcttcccc | 600 |
| agcccagaaa gttcc | 615 |

```
<210> SEQ ID NO 22
<211> LENGTH: 726
<212> TYPE: DNA
<213> ORGANISM: Artificial sequence
<220> FEATURE:
<223> OTHER INFORMATION: T cell receptor alpha chain extracellular
      domain

<400> SEQUENCE: 22
```

| gattctggag tcacacaaac cccaaagcac ctgatcacag caactggaca gcgagtgacg | 60 |
| ctgagatgct cccctaggtc tggagacctc tctgtgtact ggtaccaaca gagcctggac | 120 |
| cagggcctcc agttcctcat tcagtattat aatggagaag agagagcaaa aggaaacatt | 180 |
| cttgaacgat tctccgcaca acagttccct gacttgcact tgaactaaa cctgagctct | 240 |
| ctggagctgg gggactcagc tttgtatttc tgtgccagca gcctcggggg ggaatctgag | 300 |
| cagtacttcg gccgggcac caggctcacg gtcacagagg acctgaaaaa cgtgttccca | 360 |
| cccgaggtcg ctgtgtttga gccatcagaa gcagagatct cccacaccca aaggccaca | 420 |
| ctggtgtgcc tggccaccgg tttctacccc gaccacgtgg agctgagctg gtgggtgaat | 480 |
| gggaaggagg tgcacagtgg ggtctgcaca gacccgcagc ccctcaagga gcagcccgcc | 540 |
| ctcaatgact ccagatacgc tctgagcagc cgcctgaggg tctcggccac cttctggcag | 600 |
| gacccccgca accacttccg ctgtcaagtc cagttctacg ggctctcgga aatgacgag | 660 |
| tggacccagg atagggccaa acccgtcacc cagatcgtca gcgccgaggc ctggggtaga | 720 |
| gcagac | 726 |

```
<210> SEQ ID NO 23
<211> LENGTH: 1867
<212> TYPE: DNA
<213> ORGANISM: Artificial sequence
<220> FEATURE:
<223> OTHER INFORMATION: T cell receptor fused to porcine teschovirus-1
      2A

<400> SEQUENCE: 23
```

| gctagccgcc accatgatga agtccctgcg ggtgctgctg gtcatcctgt ggctgcagct | 60 |
| gtcctgggtc tggtcccagc agaaagaggt ggagcagaac agcggccctc tgagcgtgcc | 120 |
| cgagggcgct atcgccagcc tgaactgcac ctacagcgac agaggcagcc agagcttctt | 180 |
| ctggtacaga cagtacagcg gcaagagccc cgagctgatc atgagcatct acagcaacgg | 240 |
| cgacaaagag gacggccggt tcaccgccca gctgaacaag gccagccagt acgtgtccct | 300 |
| gctgatccgg gacagccagc ccagcgacag cgccacctac ctgtgcgccg tgaacagcga | 360 |
| ctccggctac gccctgaact tcggcaaggg caccagcctg ctggtgacac cccacattca | 420 |
| gaaccccgac cccgccgtgt accagctgcg ggacagcaag agcagcgaca agagcgtgtg | 480 |
| cctgttcacc gacttcgaca gccagaccaa cgtgtcccag agcaaggaca gcgacgtgta | 540 |
| catcaccgac aagaccgtgc tggacatgcg gagcatggac ttcaagagca cagcgccgt | 600 |
| ggcctggtcc aacaagagcg acttcgcctg cgccaacgcc ttcaacaaca gcatcatccc | 660 |
| cgaggacaca tttttcccaa gccccgagag cagctgcgca gtcaaactgg tggagaagtc | 720 |
| cttcgagaca gacaccaacc tgaacttcca gaacctgagc gtgatcggct tcagaatcct | 780 |

-continued

```
gctgctgaag gtggccggct tcaatctgct gatgaccctg cggctgtggt ccagcggcag    840
cagagccaag agaagcggat ccggcgccac caacttcagc ctgctgaagc aggccggcga    900
cgtggaggaa aaccctggcc ctaggatggg cttccggctg ctgtgctgcg tggccttctg    960
cctgctggga gccggccctg tggatagcgg cgtgacccag acccccaagc acctgatcac   1020
cgccaccggc cagagagtga ccctgcgctg cagccctaga agcggcgacc tgtccgtgta   1080
ctggtatcag cagagcctgg accagggact gcagttcctc atccagtact acaacggcga   1140
ggaacgggcc aagggcaaca tcctggaaag attcagcgcc cagcagttcc ccgacctgca   1200
cagcgagctg aacctgagca gcctggaact gggcgactcc gccctgtact tctgcgccag   1260
cagcctgggc ggcgagagcg aacagtactt cggccctggc acccggctga cggtaaccga   1320
ggacctgaag aacgtgttcc ccccagaggt ggccgtgttc gagccctctg aggccgagat   1380
cagccacacc cagaaagcca ccctggtctg cctggccacc ggcttctacc ccgaccacgt   1440
ggaactgtct tggtgggtga acggcaaaga ggtgcacagc ggcgtcagca ccgaccctca   1500
gcccctgaaa gagcagcccg ccctgaacga cagccggtac tgcctgagca gcagactgcg   1560
ggtgtccgcc accttctggc agaacccccg gaaccacttc agatgccagg tgcagttcta   1620
cggcctgagc gagaacgacg agtggaccca ggaccgggcc aagcctgtga cccagatcgt   1680
gtctgccgaa gcatgggggc gcgccgattg cggcttcaca agcgagagct accagcaggg   1740
cgtgctgagc gccaccatcc tgtacgagat cctgctgggc aaggccaccc tgtacgccgt   1800
gctggtgtcc gctctggtgc tgatggccat ggtgaaacgg aaggacagcc ggggctaata   1860
agtcgac                                                             1867
```

<210> SEQ ID NO 24
<211> LENGTH: 614
<212> TYPE: PRT
<213> ORGANISM: Artificial sequence
<220> FEATURE:
<223> OTHER INFORMATION: T cell receptor fused to porcine teschovirus-1 2A

<400> SEQUENCE: 24

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Ser Asp Ser Gly Tyr Ala Leu Asn Phe Gly Lys Gly Thr Ser
        115                 120                 125

Leu Leu Val Thr Pro His Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160
```

```
Phe Asp Ser Gln Thr Asn Val Ser Gln Ser Lys Asp Ser Asp Val Tyr
                165                 170                 175
Ile Thr Asp Lys Thr Val Leu Asp Met Arg Ser Met Asp Phe Lys Ser
                180                 185                 190
Asn Ser Ala Val Ala Trp Ser Asn Lys Ser Asp Phe Ala Cys Ala Asn
                195                 200                 205
Ala Phe Asn Asn Ser Ile Ile Pro Glu Asp Thr Phe Phe Pro Ser Pro
                210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
                260                 265                 270
Ser Ser Gly Ser Arg Ala Lys Arg Ser Gly Ser Gly Ala Thr Asn Phe
                275                 280                 285
Ser Leu Leu Lys Gln Ala Gly Asp Val Glu Glu Asn Pro Gly Pro Arg
                290                 295                 300
Met Gly Phe Arg Leu Leu Cys Cys Val Ala Phe Cys Leu Leu Gly Ala
305                 310                 315                 320
Gly Pro Val Asp Ser Gly Val Thr Gln Thr Pro Lys His Leu Ile Thr
                325                 330                 335
Ala Thr Gly Gln Arg Val Thr Leu Arg Cys Ser Pro Arg Ser Gly Asp
                340                 345                 350
Leu Ser Val Tyr Trp Tyr Gln Gln Ser Leu Asp Gln Gly Leu Gln Phe
                355                 360                 365
Leu Ile Gln Tyr Tyr Asn Gly Glu Glu Arg Ala Lys Gly Asn Ile Leu
                370                 375                 380
Glu Arg Phe Ser Ala Gln Gln Phe Pro Asp Leu His Ser Glu Leu Asn
385                 390                 395                 400
Leu Ser Ser Leu Glu Leu Gly Asp Ser Ala Leu Tyr Phe Cys Ala Ser
                405                 410                 415
Ser Leu Gly Gly Glu Ser Glu Gln Tyr Phe Gly Pro Gly Thr Arg Leu
                420                 425                 430
Thr Val Thr Glu Asp Leu Lys Asn Val Phe Pro Pro Glu Val Ala Val
                435                 440                 445
Phe Glu Pro Ser Glu Ala Glu Ile Ser His Thr Gln Lys Ala Thr Leu
450                 455                 460
Val Cys Leu Ala Thr Gly Phe Tyr Pro Asp His Val Glu Leu Ser Trp
465                 470                 475                 480
Trp Val Asn Gly Lys Glu Val His Ser Gly Val Ser Thr Asp Pro Gln
                485                 490                 495
Pro Leu Lys Glu Gln Pro Ala Leu Asn Asp Ser Arg Tyr Cys Leu Ser
                500                 505                 510
Ser Arg Leu Arg Val Ser Ala Thr Phe Trp Gln Asn Pro Arg Asn His
                515                 520                 525
Phe Arg Cys Gln Val Gln Phe Tyr Gly Leu Ser Glu Asn Asp Glu Trp
                530                 535                 540
Thr Gln Asp Arg Ala Lys Pro Val Thr Gln Ile Val Ser Ala Glu Ala
545                 550                 555                 560
Trp Gly Arg Ala Asp Cys Gly Phe Thr Ser Glu Ser Tyr Gln Gln Gly
                565                 570                 575
```

```
<210> SEQ ID NO 25
<211> LENGTH: 45
<212> TYPE: DNA
<213> ORGANISM: Artificial sequence
<220> FEATURE:
<223> OTHER INFORMATION: PCR primer

<400> SEQUENCE: 25
gaattccata tgcaaaaaga agttgaacaa aattctggac ccctc          45

<210> SEQ ID NO 26
<211> LENGTH: 36
<212> TYPE: DNA
<213> ORGANISM: Artificial sequence
<220> FEATURE:
<223> OTHER INFORMATION: PCR primer

<400> SEQUENCE: 26
ttgtcagtcg acttagagtc tctcagctgg tacacg                    36

<210> SEQ ID NO 27
<211> LENGTH: 45
<212> TYPE: DNA
<213> ORGANISM: Artificial sequence
<220> FEATURE:
<223> OTHER INFORMATION: PCR primer

<400> SEQUENCE: 27
gaattccata tggattctgg agttacacaa accccaaagc acctg          45

<210> SEQ ID NO 28
<211> LENGTH: 32
<212> TYPE: DNA
<213> ORGANISM: Artificial sequence
<220> FEATURE:
<223> OTHER INFORMATION: PCR primer

<400> SEQUENCE: 28
tagaaaccgg tggccaggca caccagtgtg gc                        32
```

Val Leu Ser Ala Thr Ile Leu Tyr Glu Ile Leu Gly Lys Ala Thr
                580                 585                 590

Leu Tyr Ala Val Leu Val Ser Ala Leu Val Leu Met Ala Met Val Lys
        595                 600                 605

Arg Lys Asp Ser Arg Gly
    610

T CELL RECEPTORS

RELATED APPLICATIONS AND INCORPORATION BY REFERENCE

This application is a divisional of U.S. application Ser. No. 15/006,224 filed Jan. 26, 2016, now allowed, which is a continuation-in-part application of international patent application Serial No. PCT/GB2014/052199 filed Jul. 18, 2014, which published as PCT Publication No. WO 2015/011450 on Jan. 29, 2015, which claims benefit of United Kingdom patent application Serial No. 1313377.2 filed Jul. 26, 2013.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Dec. 9, 2015, is named 43784_00_2005 SL.txt and is 47,533 bytes in size.

FIELD OF THE INVENTION

The present invention relates to T cell receptors (TCRs) which bind the HLA-A2 restricted FMNKFIYEI (158-166) peptide epitope derived from α Fetoprotein (AFP). Certain preferred TCRs of the invention demonstrate excellent binding characteristics and specificity profiles for this AFP epitope.

BACKGROUND OF THE INVENTION

AFP is expressed during foetal development and is the main component of foetal serum. During development the protein is produced at very high levels by the yolk sac and liver and is later repressed. AFP expression is frequently reactivated in hepatocellular carcinoma (Butterfield et al. J Immunol., 2001, Apr. 15; 166(8):5300-8) and high levels of the protein are used as a diagnostic marker for the disease.

Hepatocellular carcinoma has one of the lowest reported 5 year survival rate of all malignancies in the US, global annual incidence is 1.2 million and is likely to increase due to the pandemic of Hepatitis B and C. Treatment typically involves surgery, however this is only beneficial if carried out in the early stages of the disease. New treatments are therefore desirable.

There are four known epitopes derived from AFP: AFP158, AFP137, AFP325 and AFP542 (Butterfield et al. J Immunol., 2001, Apr. 15; 166(8):5300-8 and Butterfield et al. Cancer Res. 1999, 59: 3134-3142). The HLA-A2 restricted AFP158 peptide FMNKFIYEI (SEQ ID No: 1) provides a suitable target for novel immunotherapeutic interventions; this peptide is naturally processed and has been eluted from HepG2 (HLA-A2 positive) liver carcinoma lines and detected by mass spectrometry (Butterfield et al. J Immunol., 2001, Apr. 15; 166(8):5300-8). T cell clones have been raised against AFP158 (and AFP137) (Pichard et al. J Immunother. 2008 April; 31(3):246-53). However, T cell receptors which recognize this peptide have not been reported.

Citation or identification of any document in this application is not an admission that such document is available as prior art to the present invention.

SUMMARY OF THE INVENTION

The present invention relates to a non-naturally occurring and/or purified and/or engineered T cell receptor (TCR) having the property of binding to FMNKFIYEI (SEQ ID No: 1) HLA-A2 complex and which may comprise at least one TCR alpha chain variable domain and/or at least one TCR beta chain variable domain, the alpha chain variable domain which may comprise an amino acid sequence that has at least 90% identity to the sequence of amino acid residues 1-112 of TRAV12-2*02/TRAJ41*01/TRAC, the extracellular sequence of the parental AFP TCR alpha chain is given in FIG. 1 (SEQ ID No: 2), and/or the beta chain variable domain which may comprise an amino acid sequence that has at least 90% identity to the sequence of amino acid residues 1-112 of TRBV9*01/TRBD2/TRBJ2-7*01/TRBC2, the extracellular sequence of the parental AFP TCR alpha chain is given in FIG. 2 (SEQ ID No: 3).

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 (SEQ ID No: 2) gives the amino acid sequence of the extracellular part of the alpha chain of the parental AFP-specific TCR with gene usage TRAV12-2*02/TRAJ41*01/TRAC.

FIG. 2 (SEQ ID No: 3) gives the amino acid sequence of the extracellular part of the beta chain of the parental AFP-specific TCR with gene usage TRBV9*01/TRBD2/TRBJ2-7*01/TRBC2.

FIG. 3 (SEQ ID No: 4) gives the amino acid sequence of the alpha chain of a soluble TCR (referred to herein as the "reference TCR"). The sequence is the same as that of FIG. 1 (SEQ ID No: 2) except that a cysteine (bold and underlined) is substituted for T159 of SEQ ID No: 2 (i.e. T48 of the TRAC constant region).

FIG. 4 (SEQ ID No: 5) gives the amino acid sequence of the beta chain of a soluble TCR (referred to herein as the "reference TCR"). The sequence is the same as that of FIG. 2 (SEQ ID No: 3) except that a cysteine (bold and underlined) is substituted for S169 of SEQ ID No: 3 (i.e. S57 of the TRBC2 constant region) and A187 is substituted for C187 and D201 is substituted for N201.

FIG. 5 (SEQ ID Nos: 6-20) gives the amino acid sequence of the mutated alpha chains which may be present in TCRs of the invention. The CDR regions are underlined and amino acid changes relative to the parental AFP TCR are shaded.

FIG. 6 (SEQ ID No: 21) and (SEQ ID No: 22) gives the DNA sequences encoding the TCR alpha and beta chains shown in FIGS. 3 and 4 respectively FIG. 7 (SEQ ID No: 23) gives the DNA sequence for the parental AFP TCR gene (alpha chain-2A-beta chain construct with the Porcine teschovirus-1 2A sequence bold and underlined) for transduction of T-cells.

FIG. 8 (SEQ ID No: 24) gives the amino acid sequence of the parental AFP TCR for T-cell transduction produced from the DNA sequence of FIG. 7. The Porcine teschovirus-1 2A sequence is bold and underlined.

DETAILED DESCRIPTION OF THE INVENTION

Figure 9:
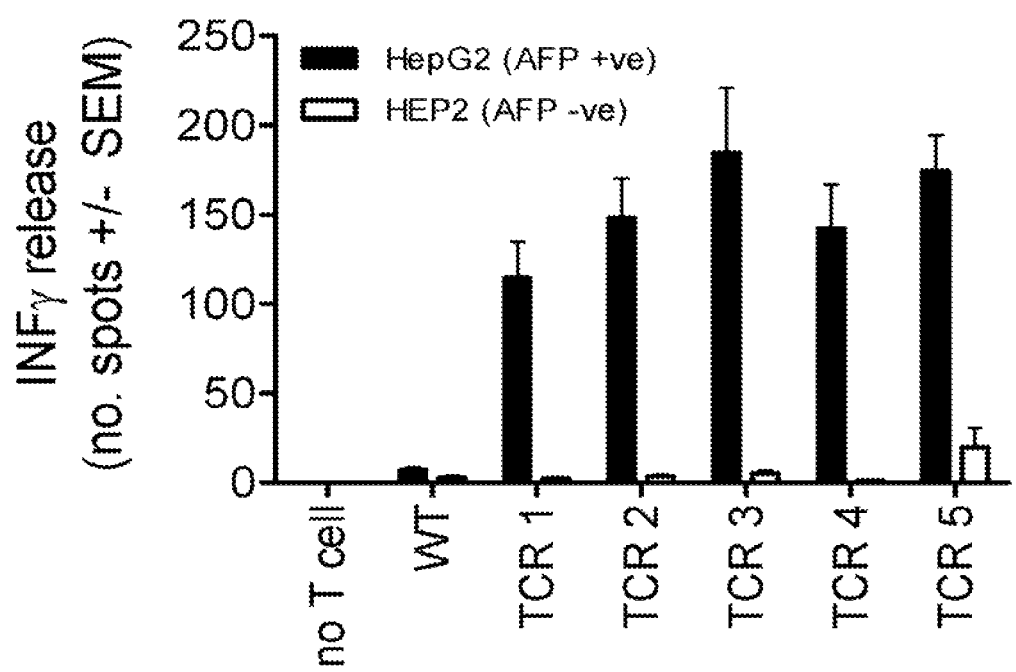
FIG. 9 shows the results of an ELISPOT assay in which IFN-γ release of AFP TCR-transduced T-cells in response to a range of target cells was assessed.

According to a first aspect of the invention, there is provided a non-naturally occurring and/or purified and/or engineered T cell receptor (TCR) having the property of binding to FMNKFIYEI (SEQ ID No: 1) HLA-A2 complex and which may comprise at least one TCR alpha chain variable domain and/or at least one TCR beta chain variable domain,
  the alpha chain variable domain which may comprise an amino acid sequence that has at least 90% identity to the sequence of amino acid residues 1-112 of SEQ ID No: 2, and/or
  the beta chain variable domain which may comprise an amino acid sequence that has at least 90% identity to the sequence of amino acid residues 1-112 of SEQ ID No: 3.

In some embodiments of the invention, the alpha chain variable domain has at least 91%, 92%, 93%, 94%, 95%, 96%, 97%, 98%, 99%, or 100% sequence identity to amino acid residues 1 to 112 of SEQ ID No: 2.

The beta chain variable domain may have at least 91%, 92%, 93%, 94%, 95%, 96%, 97%, 98%, 99%, or 100% sequence identity to amino acid residues 1 to 112 of SEQ ID No: 3.

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain may comprise variable, joining and constant regions, and the beta chain also usually contains a short diversity region between the variable and joining regions, but this diversity region is often considered as part of the joining region. Each variable region may comprise three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The α and β chains of αβ TCR's are generally regarded as each having two "domains" or "regions", namely variable and constant domains/regions. The terms "domain(s)" and "region(s)" are used interchangeably herein. The variable domain consists of a concatenation of variable region and joining region. In the present specification and claims, the term "TCR alpha variable domain" therefore refers to the concatenation of TRAV and TRAJ regions, and the term TCR alpha constant domain refers to the extracellular TRAC region, or to a C-terminal truncated TRAC sequence. Likewise the term "TCR beta variable domain" refers to the concatenation of TRBV and TRBD/TRBJ regions, and the term TCR beta constant domain refers to the extracellular TRBC region, or to a C-terminal truncated TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

Figure 1:
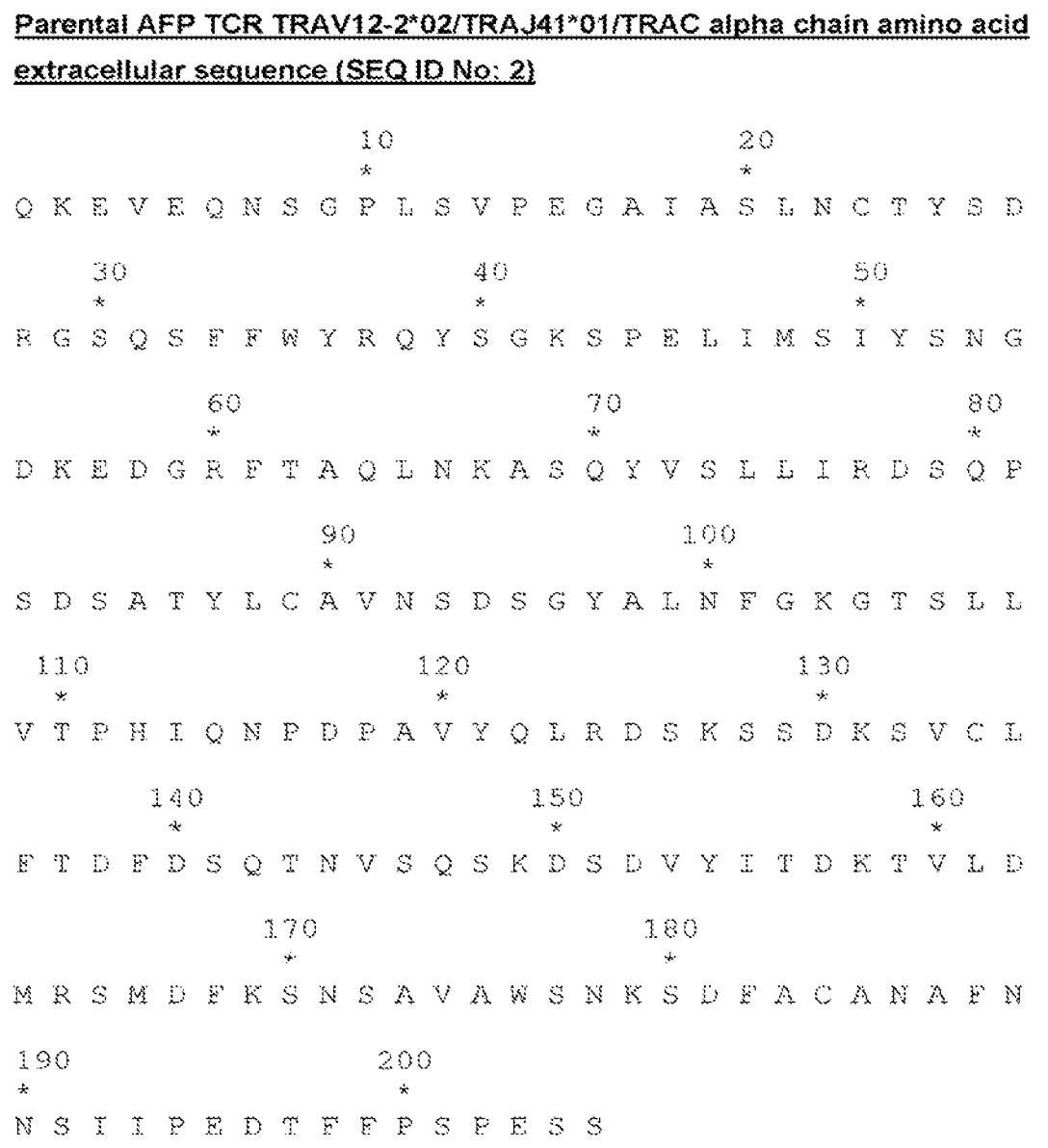

SEQ ID Nos: 2 and 3 are, respectively, the alpha and beta chain extracellular sequences of what is referred to herein as the "parental" AFP TCR. The parental AFP TCR has the following alpha and beta chain usage:
  Alpha chain: TRAV12-2*02/TRAJ41*01/TRAC (the extracellular sequence of the parental AFP TCR alpha chain is given in FIG. 1 (SEQ ID No: 2). The CDRs are defined by amino acids 27-32 (CDR1), 50-55 (CDR2) and 90-101 (CDR3) of SEQ ID NO: 2.

Figure 2:
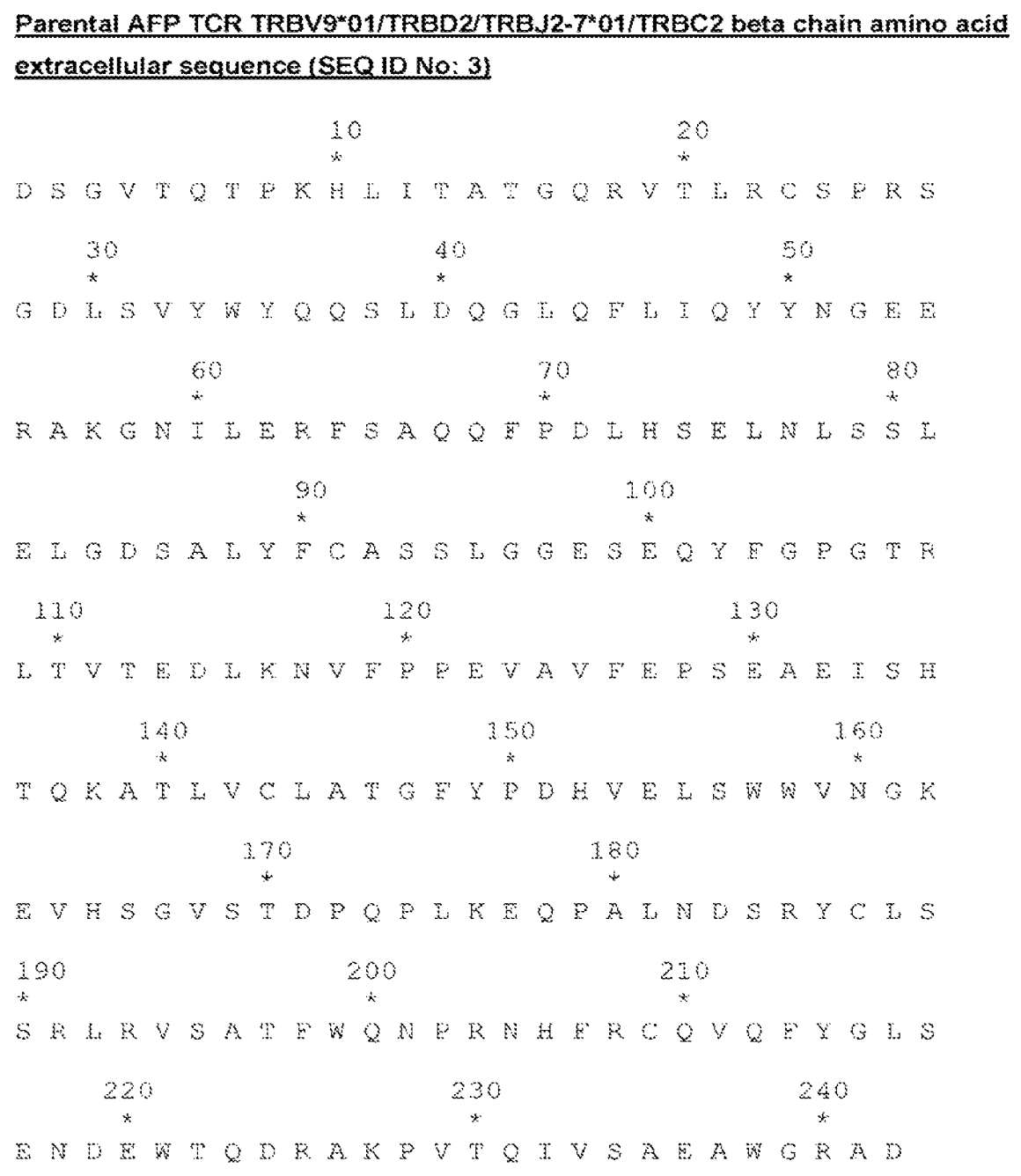

Beta chain: TRBV9*01/TRBD2/TRBJ2-7*01/TRBC2 (the extracellular sequence of the parental AFP TCR alpha chain is given in FIG. 2 (SEQ ID No: 3). The CDRs are defined by amino acids 27-31 (CDR1), 49-54 (CDR2) and 92-102 (CDR3) of SEQ ID NO: 3.

(Note, the terms '*01' and '*02' indicate there is more than one allelic variant for this sequence, as designated by IMGT nomenclature, and that it is the *01/*02 variant which is present in the TCR clone referred to above. Note also that the absence of a "*" qualifier means that only one allele is known for the relevant sequence.)

Figure 3:
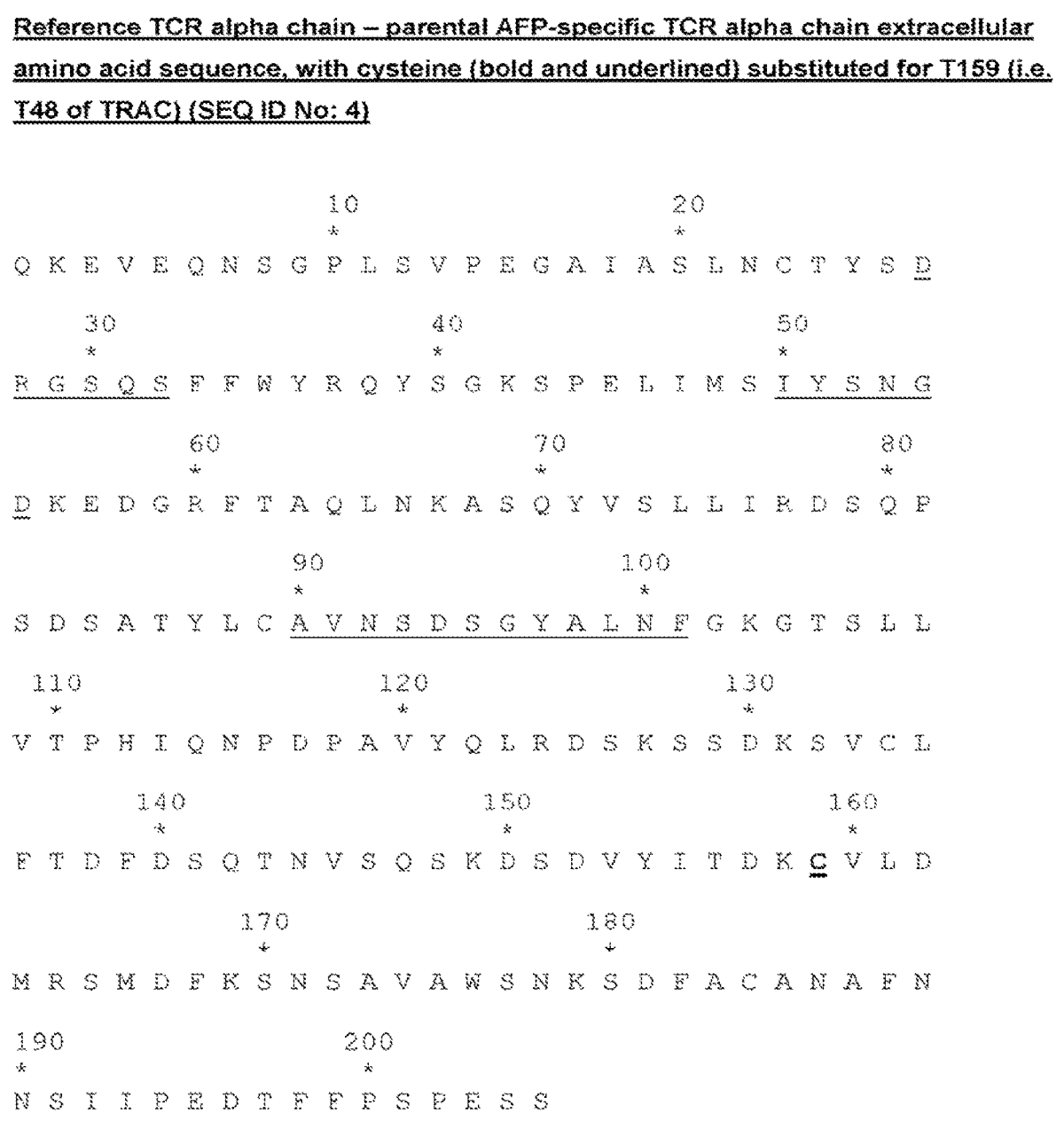

For the purpose of providing a reference TCR against which the binding profile of mutated TCRs of the invention may be compared, it is convenient to use the soluble TCR having the extracellular sequence of the AFP TCR alpha chain given in FIG. 3 (SEQ ID No: 4) and the extracellular sequence of the AFP TCR beta chain given in FIG. 4 (SEQ ID No: 5). That TCR is referred to herein as the "the reference TCR" or "the reference AFP TCR". Note that SEQ ID No: 4 is identical to the parental alpha chain extracellular sequence SEQ ID No: 2 except that C159 has been substituted for T159 (i.e. T48 of TRAC). Likewise SEQ ID No: 5 is identical to the parental beta chain extracellular sequence SEQ ID No: 3 except that C169 has been substituted for S169 (i.e. S57 of TRBC2), A187 has been substituted for C187 and D201 has been substituted for N201. These cysteine substitutions relative to the parental AFP alpha and beta chain extracellular sequences enable the formation of an interchain disulfide bond which stabilises the refolded soluble TCR, ie the TCR formed by refolding extracellular alpha and beta chains. Use of the stable disulfide linked soluble TCR as the reference TCR enables more convenient assessment of binding affinity and binding half-life.

TCRs of the invention may be transformed into T cells, rendering them capable of destroying cells presenting AFP HLA-A2 complex, for administration to a patient in the treatment process known as adoptive therapy. For this purpose, it would be desirable if the TCRs had a higher affinity and/or a slower off-rate for the peptide-HLA complex than native TCRs specific for that complex. Dramatic increases in affinity have been associated with a loss of antigen specificity in TCR gene-modified CD8 T cells, which could result in the nonspecific activation of these TCR-transfected CD8 cells. Therefore, TCRs having a somewhat higher affinity and/or a slower off-rate for the peptide-HLA complex than native TCRs specific for that complex, but not a dramatically higher affinity and/or dramatically slower off-rate for the peptide-HLA complex than native TCRs, would be preferred for adoptive therapy (see Zhao et al., (2007) *J Immunol.* 179: 5845-54; Robbins et al., (2008) *J Immunol.* 180: 6116-31; and WO2008/038002).

Embodiments of the invention include TCRs which are mutated relative to the parental AFP TCR. Mutated TCRs may comprise an alpha chain variable domain that includes a mutation in one or more of the amino acids corresponding to: 31Q, 32S, 94D, 95S, 96G, 97Y, and 98A, with reference to the numbering shown in SEQ ID No: 2. For example, the alpha chain variable domain may have one or more of the following mutations:

| Residue no. | | |
| --- | --- | --- |
| 31Q | F | Y |
| 32S | A | |
| 94D | Q | |
| 95S | N | |
| 96G | S | |
| 97Y | V | |
| 98A | S | |

The numbering used above is the same as that shown in FIG. 1 (SEQ ID No: 2)

The alpha chain variable domain may comprise an amino acid sequence having at least 90%, 91%, 92%, 93%, 94%, 95%, 96%, 97%, 98%, 99%, or 100% identity to residues 1-112 of any one of SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, SEQ ID No: 16, SEQ ID No: 17, SEQ ID No: 18, SEQ ID No: 19 and SEQ ID No: 20, and preferably, the amino acid sequence also has at least 90% identity to residues 1-112 of SEQ ID No: 2. The amino acids underlined in FIG. 5 may be invariant.

In one embodiment, the TCR may comprise an alpha chain variable domain which may comprise Q1 to H112 of SEQ ID No: 11, SEQ ID No: 12 or SEQ ID No: 13, and/or a beta chain variable domain which may comprise D1 to T112 of SEQ ID NO: 3.

Mutations can be carried out using any appropriate method including, but not limited to, those based on polymerase chain reaction (PCR), restriction enzyme-based cloning, or ligation independent cloning (LIC) procedures. These methods are detailed in many of the of the standard molecular biology texts. For further details regarding polymerase chain reaction (PCR) and restriction enzyme-based cloning, see Sambrook & Russell, (2001) Molecular Cloning—A Laboratory Manual (3$^{rd}$ Ed.) CSHL Press. Further information on ligation independent cloning (LIC) procedures can be found in Rashtchian, (1995) Curr Opin Biotechnol 6(1): 30-6.

Also within the scope of the invention are phenotypically silent variants of any TCR disclosed herein. As used herein the term "phenotypically silent variants" is understood to refer to those TCRs which have a $K_D$ and/or binding half-life for the FMNKFIYEI (SEQ ID No: 1) HLA-A2 complex within the ranges of KDs and binding half-lives described below. For example, as is known to those skilled in the art, it may be possible to produce TCRs that incorporate changes in the constant and/or variable domains thereof compared to those detailed above without altering the affinity for the interaction with the FMNKFIYEI (SEQ ID No: 1) HLA-A2 complex. Such trivial variants are included in the scope of this invention. Those TCRs in which one or more conservative substitutions have been made also form part of this invention.

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present invention.

Native TCRs exist in heterodimeric αβ or γδ forms. However, recombinant TCRs consisting of αα or ββ homodimers have previously been shown to bind to peptide MHC molecules. Therefore, the TCR of the invention may be a heterodimeric αβ TCR or may be an αα or ββ homodimeric TCR.

For use in adoptive therapy, an αβ heterodimeric TCR may, for example, be transfected as full length chains having both cytoplasmic and transmembrane domains. In certain embodiments TCRs of the invention may have an introduced disulfide bond between residues of the respective constant domains, as described, for example, in WO 2006/000830.

TCRs of the invention, particularly alpha-beta heterodimeric TCRs, may comprise an alpha chain TRAC constant domain sequence and/or a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR.

TCRs of the invention may be in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the invention may have an introduced disulfide bond between residues of the respective constant domains, as described in WO 2004/033685.

The TCRs of the invention have the property of binding the FMNKFIYEI (SEQ ID No: 1) HLA-A2 complex. Certain TCRs of the invention have been found to be highly suitable for use in adoptive therapy. Such TCRs may have a $K_D$ for the complex of less than the parental AFP TCR, for example from about 1 μM to about 21 μM and/or have a binding half-life (T½) for the complex in the range of from less than 0.5 seconds to about 2 seconds. Increasing the binding affinity of a native TCR often reduces the selectivity of the TCR for its peptide-MHC ligand, and this is demonstrated in Zhao Yangbing et al., (*J. Immunol*, 2007 179: 9, p 5845-5854). However, certain TCRs of the invention remain selective for the FMNKFIYEI HLA-A2 complex, despite, in some embodiments, having higher binding affinity than the parental AFP TCR (see Example 6).

Binding affinity (inversely proportional to the equilibrium constant $K_D$) and binding half-life (expressed as T½) can be determined by any appropriate method. It will be appreciated that doubling the affinity of a TCR results in halving the $K_D$. T½ is calculated as ln 2 divided by the off-rate ($k_{off}$). So doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues. Therefore it is to be understood that a given TCR has an improved binding affinity for, and/or a binding half-life for the parental TCR if a soluble form of that TCR has the said characteristics. Preferably the binding affinity or binding half-life of a given TCR is measured several times, for example 3 or more times, using the same assay protocol, and an average of the results is taken. In a preferred embodiment these measurements are made using the Surface Plasmon Resonance (BIAcore) method of Example 3 herein.

In a further aspect, the present invention provides nucleic acid encoding a TCR of the invention. In some embodiments, the nucleic acid is cDNA. In some embodiments, the invention provides nucleic acid which may comprise a sequence encoding an α chain variable domain of a TCR of the invention. In some embodiments, the invention provides nucleic acid which may comprise a sequence encoding a β chain variable domain of a TCR of the invention. In some embodiments, the invention provides nucleic acid which may comprise a sequence encoding both an α chain variable domain of a TCR of the invention and a β chain variable domain of a TCR of the invention. The nucleic acid may be non-naturally occurring and/or purified and/or engineered.

In another aspect, the invention provides a vector which may comprise nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which may comprise nucleic acid encoding the alpha chain of a TCR of the invention, and a second expression vector which may comprise nucleic acid encoding the beta chain of a TCR of the invention. Such cells are particularly useful in adoptive therapy. The cells may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancers such as those of the pancreas and liver. As will be known to those skilled in the art, there are a number of suitable methods by which adoptive therapy can be carried out (see for example Rosenberg et al., (2008) Nat Rev Cancer 8(4): 299-308).

As is well-known in the art TCRs of the invention may be subject to post-translational modifications when expressed by transfected cells. Glycosylation is one such modification, which may comprise the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e oligosaccharide type, covalent linkage and total number of attachments) can influence protein function. Therefore, when producing recombinant proteins, controlling glycosylation is often desirable. Glycosylation of transfected TCRs may be controlled by mutations of the transfected gene (Kuball J et al. (2009), J Exp Med 206(2):463-475). Such mutations are also encompassed in this invention.

The TCR of the invention may be associated with a detectable label, a therapeutic agent or a PK modifying moiety.

Certain TCRs of the invention may be in soluble form (i.e. having no transmembrane or cytoplasmic domains). For stability, TCRs of the invention, and preferably soluble heterodimeric TCRs, may have an introduced disulfide bond between residues of the respective constant domains, as described, for example, in WO 03/020763. Some soluble TCRs of the invention are useful for making fusion proteins which can be used for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting the FMNKFIYEI (SEQ ID No 1) HLA-A2 complex; a therapeutic agent; or a PK modifying moiety (for example by PEGylation).

Detectable labels for diagnostic purposes include for instance, fluorescent labels, radiolabels, enzymes, nucleic acid probes and contrast reagents.

Therapeutic agents which may be associated with the TCRs of the invention include immunomodulators, radioactive compounds, enzymes (perforin for example) or chemotherapeutic agents (cis-platin for example). To ensure that toxic effects are exercised in the desired location the toxin could be inside a liposome linked to a TCR so that the compound is released slowly. This will prevent damaging effects during the transport in the body and ensure that the toxin has maximum effect after binding of the TCR to the relevant antigen presenting cells.

Other suitable therapeutic agents include:
- small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;
- peptide cytotoxins, i.e. proteins or fragments thereof with the ability to kill mammalian cells. For example, ricin, diphtheria toxin, pseudomonas bacterial exotoxin A, DNase and RNase;
- radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;
- immuno-stimulants, i.e. immune effector molecules which stimulate immune response. For example, cytokines such as IL-2 and IFN-γ, Superantigens and mutants thereof;
- TCR-HLA fusions;
- chemokines such as IL-8, platelet factor 4, melanoma growth stimulatory protein, etc;
- antibodies or fragments thereof, including anti-T cell or NK cell determinant antibodies (e.g. anti-CD3, anti-CD28 or anti-CD16);
- alternative protein scaffolds with antibody like binding characteristics complement activators;
- xenogeneic protein domains, allogeneic protein domains, viral/bacterial protein domains, viral/bacterial peptides.

For administration to patients, the TCRs or cells of the invention may be provided in a pharmaceutical composition together with one or more pharmaceutically acceptable carriers or excipients. Cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carrier(s) or excipient(s) under sterile conditions.

TCRs, pharmaceutical compositions, vectors, nucleic acids and cells of the invention may be provided in substantially pure form, for example at least 50%, at least 60%, at least 70%, at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
- a non-naturally occurring and/or purified and/or engineered TCR which binds the FMNKFIYEI peptide presented as a peptide-HLA-A2 complex, or a cell expressing and/or presenting such a TCR, for use in medicine, preferably in a method of treating cancer. The method may comprise adoptive therapy;
- the use of a TCR which binds the FMNKFIYEI peptide presented as a peptide-HLA-A2 complex, or a cell expressing and/or presenting such a TCR, in the manufacture of a medicament for treating cancer;
- a method of treating cancer in a patient, which may comprise administering to the patient a TCR which binds the FMNKFIYEI peptide presented as a peptide-HLA-A2 complex, or a cell expressing and/or presenting such a TCR.

It is preferred that the TCR which binds the FMNKFIYEI peptide presented as a peptide-HLA-A2 complex is a TCR of the invention.

Preferred features of each aspect of the invention are as for each of the other aspects mutatis mutandis. The published documents mentioned herein are incorporated to the fullest extent permitted by law. Citation or identification of any document in this application is not an admission that such document is available as prior art to the present invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Cloning of the Parental AFP TCR Alpha and Beta Chain Variable Region Sequences into pGMT7-Based Expression Plasmids The reference AFP TCR variable alpha and TCR variable beta domains were PCR amplified from total cDNA isolated from an AFP T cell clone. In the case of the alpha chain, an alpha chain variable region sequence specific oligonucleotide A1 gaattccatatgcaaaagaagttgaacaaaattctggaccccctc (SEQ ID No: 25) which encodes the restriction site NdeI and an alpha chain constant region sequence specific oligonucleotide A2 ttgtcagtcgacttagagtctctcagctggtacacg (SEQ ID No: 26) which encodes the restriction site SalI are used to amplify the alpha chain variable domain. In the case of the beta chain, a beta chain variable region sequence specific oligonucleotide B1 gaattccatatggattctggagttacacaaaccccaaagcacctg (SEQ ID No: 27) which encodes the restriction site NdeI and a beta chain constant region sequence specific oligonucleotide B2 tagaaaccggtggccaggcacaccagtgtggc (SEQ ID No: 28) which encodes the restriction site AgeI are used to amplify the beta chain variable domain.

The alpha and beta variable domains were cloned into pGMT7-based expression plasmids containing either Cα or Cβ by standard methods described in (Molecular Cloning a Laboratory Manual Third edition by Sambrook and Russell). Plasmids were sequenced using an Applied Biosystems 3730xl DNA Analyzer.

The DNA sequences encoding the TCR alpha chain cut with NdeI and SalI were ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI.

Ligation

Ligated plasmids were transformed into competent *E. coli* strain XL1-blue cells and plated out on LB/agar plates containing 100 µg/ml ampicillin. Following incubation overnight at 37° C., single colonies are picked and grown in 10 ml LB containing 100 µg/ml ampicillin overnight at 37° C. with shaking. Cloned plasmids were purified using a Miniprep kit (Qiagen) and the plasmids were sequenced using an Applied Biosystems 3730xl DNA Analyzer.

FIGS. 3 and 4 show respectively the reference AFP TCR α and β chain extracellular amino acid sequences (SEQ ID Nos: 4 and 5 respectively) produced from the DNA sequences of FIG. 7 (SEQ ID No: 21) (SEQ ID No: 22) respectively. Note that, relative to the parental TCR, cysteines were substituted in the constant regions of the alpha and beta chains to provide an artificial inter-chain disulphide bond on refolding to form the heterodimeric TCR. The introduced cysteines are shown in bold and underlined.

Example 2

Expression, Refolding and Purification of Soluble Parental AFP TCR

The expression plasmids containing the TCR α-chain and β-chain respectively, as prepared in Example 1, were transformed separately into *E. coli* strain BL21pLysS, and single ampicillin-resistant colonies were grown at 37° C. in TYP (ampicillin 100 µg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster® (Novagen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 15 mg of TCR β chain and 15 mg of TCR α chain solubilised inclusion bodies were thawed from frozen stocks and diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectra/Por® 1 membrane (Spectrum; Product No. 132670) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS® 50HQ anion exchange column and eluting bound protein with a gradient of 0-500 mM NaCl in 10 mM Tris pH 8.1 over 50 column volumes using an Akta® purifier (GE Healthcare). Peak fractions were pooled and a cocktail of protease inhibitors (Calbiochem) were added. The pooled fractions were then stored at 4° C. and analysed by Coomassie-stained SDS-PAGE before being pooled and concentrated. Finally, the soluble TCR was purified and characterised using a GE Healthcare Superdex® 75HR gel filtration column pre-equilibrated in PBS buffer (Sigma). The peak eluting at a relative molecular weight of approximately 50 kDa was pooled and concentrated prior to characterisation by BIAcore® surface plasmon resonance analysis.

Example 3

Binding Characterisation

BIAcore Analysis

A surface plasmon resonance biosensor (BIAcore® 3000) can be used to analyse the binding of a soluble TCR to its peptide-MHC ligand. This is facilitated by producing soluble biotinylated peptide-HLA ("pHLA") complexes which can be immobilised to a streptavidin-coated binding surface (sensor chip). The sensor chips may comprise four individual flow cells which enable simultaneous measurement of T-cell receptor binding to four different pHLA complexes. Manual injection of pHLA complex allows the precise level of immobilised class I molecules to be manipulated easily.

Biotinylated class I HLA-A*02 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*02-heavy chain was expressed with a C-terminal biotinylation tag which replaces the transmembrane and cytoplasmic domains of the protein in an appropriate construct. Inclusion body expression levels of ~75 mg/litre bacterial culture were obtained. The MHC light-chain or β2-microglobulin was also expressed as inclusion bodies in E. coli from an appropriate construct, at a level of ~500 mg/litre bacterial culture.

E. coli cells were lysed and inclusion bodies were purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/litre heavy chain, 30 mg/litre β2m into 0.4 M L-Arginine, 100 mM Tris pH 8.1, 3.7 mM cystamine dihydrochloride, 6.6 mM cysteamine hydrochloride, 4 mg/L of the AFP peptide required to be loaded by the HLA-A*02 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. The protein solution was then filtered through a 1.5 µm cellulose acetate filter and loaded onto a POROS® 50HQ anion exchange column (8 ml bed volume). Protein was eluted with a linear 0-500 mM NaCl gradient in 10 mM Tris pH 8.1 using an Akta® purifier (GE Healthcare). HLA-A*02-peptide complex eluted at approximately 250 mM NaCl, and peak fractions were collected, a cocktail of protease inhibitors (Calbiochem) was added and the fractions were chilled on ice.

Biotinylation tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM $MgCl_2$, and 5 µg/ml BirA enzyme (purified according to O'Callaghan et al. (1999) Anal. Biochem. 266: 9-15). The mixture was then allowed to incubate at room temperature overnight.

The biotinylated pHLA-A*01 molecules were purified using gel filtration chromatography. A GE Healthcare Superdex® 75 HR 10/30 column was pre-equilibrated with filtered PBS and 1 ml of the biotinylation reaction mixture was loaded and the column was developed with PBS at 0.5 ml/min using an Akta® purifier (GE Healthcare). Biotinylated pHLA-A*02 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*02 molecules were stored frozen at −20° C.

The BIAcore® 3000 surface plasmon resonance (SPR) biosensor measures changes in refractive index expressed in response units (RU) near a sensor surface within a small flow cell, a principle that can be used to detect receptor ligand interactions and to analyse their affinity and kinetic parameters. The BIAcore® experiments were performed at a temperature of 25° C., using PBS buffer (Sigma, pH 7.1-7.5) as the running buffer and in preparing dilutions of protein samples. Streptavidin was immobilised to the flow cells by standard amine coupling methods. The pHLA complexes were immobilised via the biotin tag. The assay was then performed by passing soluble TCR over the surfaces of the different flow cells at a constant flow rate, measuring the SPR response in doing so.

Equilibrium Binding Constant

The above BIAcore® analysis methods were used to determine equilibrium binding constants. Serial dilutions of the disulfide linked soluble heterodimeric form of the reference AFP TCR were prepared and injected at constant flow rate of 5 µl min$^{-1}$ over two different flow cells; one coated with ~1000 RU of specific HLA-A*02 complex, the second coated with ~1000 RU of non-specific HLA-A2-peptide complex. Response was normalised for each concentration using the measurement from the control cell. Normalised data response was plotted versus concentration of TCR sample and fitted to a non-linear curve fitting model in order to calculate the equilibrium binding constant, $K_D$ (Price & Dwek, Principles and Problems in Physical Chemistry for Biochemists ($2^{nd}$ Edition) 1979, Clarendon Press, Oxford). The disulfide linked soluble form of the reference AFP TCR (Example 2) demonstrated a $K_D$ of approximately 754 µM. From the same BIAcore® data the T½ was approximately <0.5 s.

Kinetic Parameters

The above BIAcore® analysis methods were also used to determine equilibrium binding constants and off-rates.

For high affinity TCRs (see Example 4 below) $K_D$ was determined by experimentally measuring the dissociation rate constant, $k_{off}$, and the association rate constant, $k_{on}$. The equilibrium constant $K_D$ was calculated as $k_{off}/k_{on}$.

TCR was injected over two different cells one coated with ~1000 RU of FMNKFIYEI HLA-A*02 complex, the second coated with ~1000 RU of non-specific HLA-A2-peptide complex. Flow rate was set at 50 µl/min. Typically 250 µl of TCR at ~1 µM concentration was injected. Buffer was then flowed over until the response had returned to baseline or >2 hours had elapsed. Kinetic parameters were calculated using BIAevaluation® software. The dissociation phase was fitted to a single exponential decay equation enabling calculation of half-life.

Example 4

Preparation of Mutated TCRs of the Invention

Phage display is one means by which libraries of AFP TCR variants can be generated in order to identify higher affinity mutants. The TCR phage display and screening methods described in (Li et al, (2005) Nature Biotech 23 (3): 349-354) were applied to the parental AFP TCR of Example 1.

TCRs with improved binding compared to the parental AFP TCR were identified, having one or more mutations in the alpha chain variable domain amino acid residues 31Q, 32S, 94D, 95S, 96G, 97Y, and 98A (using the numbering shown in SEQ ID No: 2). Specific examples of the amino acid sequences of the variable regions of the alpha chains (SEQ ID Nos: 6 to 20) of higher affinity TCRs are shown in FIG. 5. These alpha chains are mutated in CDR1 and/or CDR3.

Expression plasmids containing the TCR α-chain and β-chain respectively for the following TCRs of the invention were prepared as in Example 1:

| TCR ID | Alpha Chain SEQ ID No | Beta Chain SEQ ID No |
|---|---|---|
| Parental | 2 | 3 |
| ADB327 | 6 | 3 |
| ADB329 | 7 | 3 |
| ADB330 | 8 | 3 |
| ADB331 | 9 | 3 |
| ADB328 | 10 | 3 |
| ADB352 | 11 | 3 |
| ADB350 | 12 | 3 |
| ADB332 | 13 | 3 |
| ADB351 | 14 | 3 |

| TCR ID | Alpha Chain SEQ ID No | Beta Chain SEQ ID No |
|---|---|---|
| ADB349 | 15 | 3 |
| ADB353 | 16 | 3 |
| ADB326 | 17 | 3 |
| ADB333 | 18 | 3 |
| ADB334 | 19 | 3 |
| ADB335 | 20 | 3 |

The plasmids were transformed separately into *E. coli* strain BL21pLysS, and single ampicillin-resistant colonies grown at 37° C. in TYP (ampicillin 100 µg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster® (Novagen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 10 mg of TCR β chain and 10 mg of TCR α chain solubilised inclusion bodies for each TCR of the invention were diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectra/Por® 1 membrane (Spectrum; Product No. 132670) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS® 50HQ anion exchange column and eluting bound protein with a gradient of 0-500 mM NaCl in 10 mM Tris pH 8.1 over 15 column volumes using an Akta® purifier (GE Healthcare). The pooled fractions were then stored at 4° C. and analysed by Coomassie-stained SDS-PAGE before being pooled and concentrated. Finally, the soluble TCRs were purified and characterised using a GE Healthcare Superdex® 75HR gel filtration column pre-equilibrated in PBS buffer (Sigma). The peak eluting at a relative molecular weight of approximately 50 kDa was pooled and concentrated prior to characterisation by BIAcore® surface plasmon resonance analysis.

The affinity profiles of the thus-prepared TCRs for the AFP epitope were assessed using the method of Example 3, and compared with the reference TCR. The results are set forth in the following table:

| TCR alpha chain extracellular domain | T½ (s) | KD µM |
|---|---|---|
| Parental | <0.5 | 754 |
| ADB327 | <0.5 | 489 |
| ADB329 | <0.5 | 356 |
| ADB330 | <0.5 | 178 |
| ADB331 | <0.5 | 79.5 |
| ADB328 | <0.5 | 33.3 |
| ADB352 | <0.5 | 20.1 |
| ADB350 | 0.8 | 11.0 |
| ADB332 | 0.7 | 10.6 |
| ADB351 | 0.8 | 8.0 |
| ADB349 | 1.8 | 4.55 |
| ADB353 | 1.5 | 4.17 |
| ADB326 | 1.5 | 1.50 |
| ADB333 | 3.8 | 0.71 |
| ADB334 | 4.3 | 0.52 |
| ADB335 | 13.9 | 0.31 |

Example 5

Transfection of T-Cells with Parental and Variant AFP TCRs (a) Lentiviral Vector Preparation by Express-in Mediated Transient Transfection of 293T Cells A 3rd generation lentiviral packaging system was used to package lentiviral vectors containing the gene encoding the desired TCR. 293T cells were transfected with 4 plasmids (one lentiviral vector containing the TCR alpha chain-P2A-TCR beta chain single ORF gene described in Example 5c (below), and 3 plasmids containing the other components necessary to construct infective but non-replicative lentiviral particles) using Express-In mediated transfection (Open Biosystems).

For transfection take one T150 flask of 293T cells in exponential growth phase, with cells evenly distributed on the plate, and slightly more than 50% confluent. Bring Express-In aliquots to room temperature. Place 3 ml Serum-Free Medium (RPMI 1640+10 mM HEPES) in a sterile 15 ml conical tube. Add 174 µl of Express-In Reagent directly into the Serum-Free Medium (this provides for a 3.6:1 weight ratio of Reagent to DNA). Mix thoroughly by inverting tubes 3-4 times and incubate at room temperature for 5-20 minutes.

In a separate 1.5 ml microtube, add 15 µg plasmid DNA to premixed packaging mix aliquots (containing 18 µg pRSV.REV (Rev expression plasmid), 18 µg pMDLg/p.RRE (Gag/Pol expression plasmid), 7 µg pVSV-G (VSV glycoprotein expression plasmid), usually ~22 and pipette up and down to ensure homogeneity of the DNA mix. Add ~1 ml of Express-In/Serum-Free Medium to the DNA mix drop wise then pipette up and down gently before transferring back to the remainder of the Express-In/Serum-Free Medium. Invert tube 3-4 times and incubate at room temperature for 15-30 minutes.

Remove old culture medium from flask of cells. Add Express-In/medium/DNA (3 ml) complex to flask direct into the bottom of an upright flask of 293T cells. Slowly, place the flask flat to cover the cells and very gently rock the flask to ensure even distribution. After 1 minute add 22 ml fresh culture medium (R10+HEPES: RPMI 1640, 10% heat-inactivated FBS, 1% Pen/Strep/L-glutamine, 10 mM HEPES) and carefully return to incubator. Incubate overnight at 37° C./5% CO2. After 24 hours, proceed to harvest the medium containing packaged lentiviral vectors.

To harvest the packaged lentiviral vectors, filter the cell culture supernatent through a 0.45 micron nylon syringe filter, centrifuge the culture medium at 10,000 g for 18 hours (or 112,000 g for 2 hours), remove most of the supernatant (taking care not to disturb the pellet) and resuspend the pellet in the remaining few ml of supernatant (usually about 2 ml from a 31 ml starting volume per tube). Snap freeze on dry ice in 1 ml aliquots and store at −80° C.

(b) Transduction of T Cells with Packaged Lentiviral Vectors Containing Gene of Interest Prior to transduction with the packaged lentiviral vectors, human T cells (CD8 or CD4 or both depending on requirements) are isolated from the blood of healthy volunteers. These cells are counted and incubated overnight in R10 containing 50 U/ml IL-2 at $1 \times 10^6$ cells per ml (0.5 ml/well) in 48 well plates with pre-washed anti-CD3/CD28 antibody-coated microbeads (Dynabeads® T cell expander, Invitrogen) at a ratio of 3 beads per cell.

After overnight stimulation, 0.5 ml of neat packaged lentiviral vector is added to the desired cells. Incubate at 37° C./5% CO2 for 3 days. 3 days post-transduction count cells and dilute to $0.5 \times 10^6$ cells/ml. Add fresh medium containing IL-2 as required. Remove beads 5-7 days post-transduction. Count cells and replace or add fresh medium containing IL-2 at 2 day intervals. Keep cells between $0.5 \times 10^6$ and $1 \times 10^6$ cells/ml. Cells can be analysed by flow cytometry from day 3 and used for functional assays (e.g. ELISpot for IFNγ release, see Example 6) from day 5. From day 10, or when cells are slowing division and reduced in size, freeze cells in aliquots of at least $4 \times 10^6$ cells/vial (at $1 \times 10^7$ cells/ml in 90% FBS/10% DMSO) for storage.

(c) Parental TCR Gene for T-Cell Transfection by Methods (a) and (b) Above

FIG. 7 is a DNA sequence (SEQ ID No: 23) encoding the parental AFP TCR (codon-optimised for maximal human cell expression). It is a full length alpha chain—Porcine teschovirus-1 2A—full length beta chain single open reading frame construct. The 2A sequence is underlined, and is preceded by nucleotides encoding a furin cleavage site to assist proteolytic removal of the 2A sequence (discussed further below in relation to FIG. 8 (SEQ ID No: 24). Peptide bond skipping during protein translation of the mRNA at the 3' end of the 2A sequence produces two proteins: 1) alpha TCR chain-2A fusion, 2) beta TCR chain. SEQ ID No: 23 includes NheI and SalI restriction sites (underlined).

Figure 8:
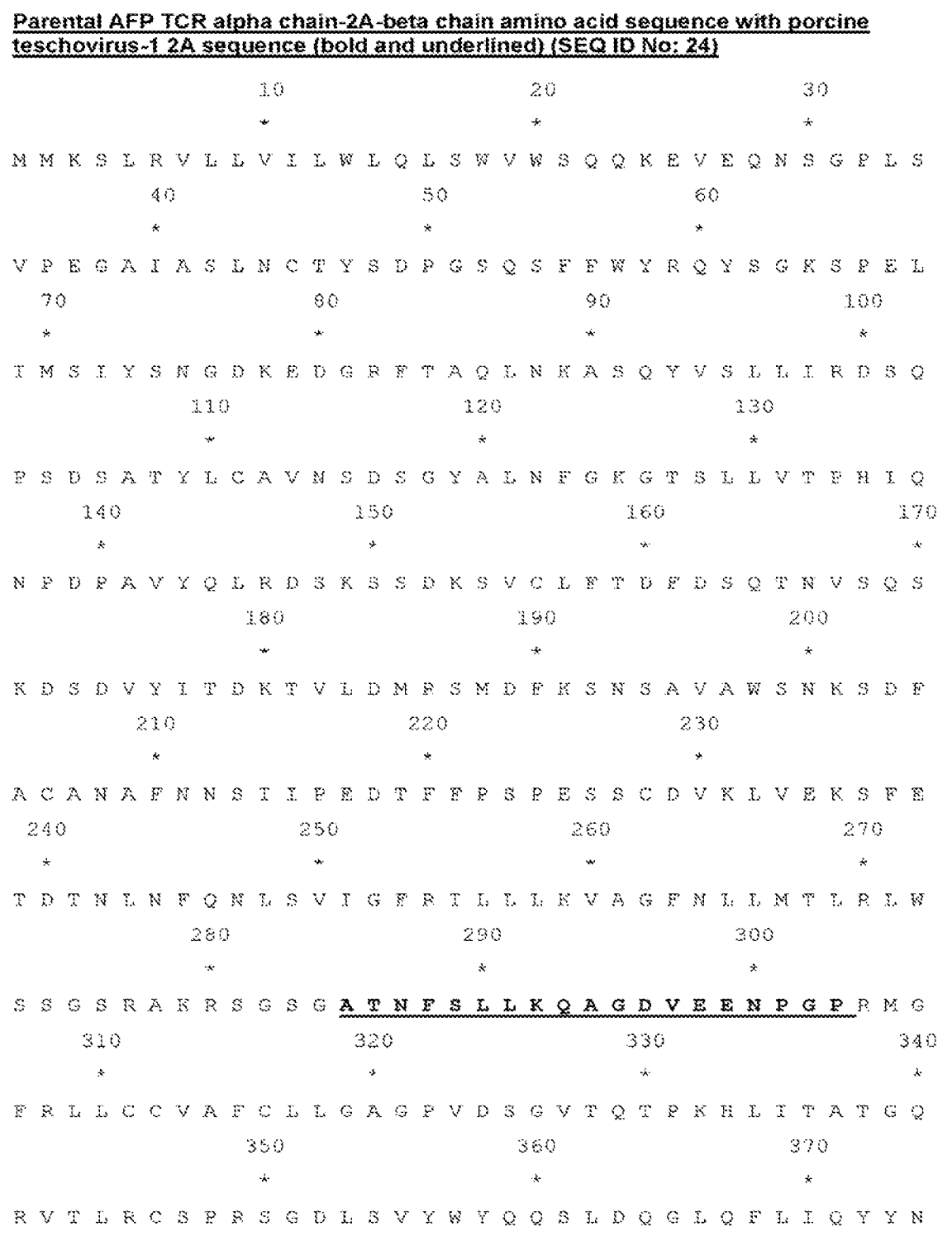
Figure 8:
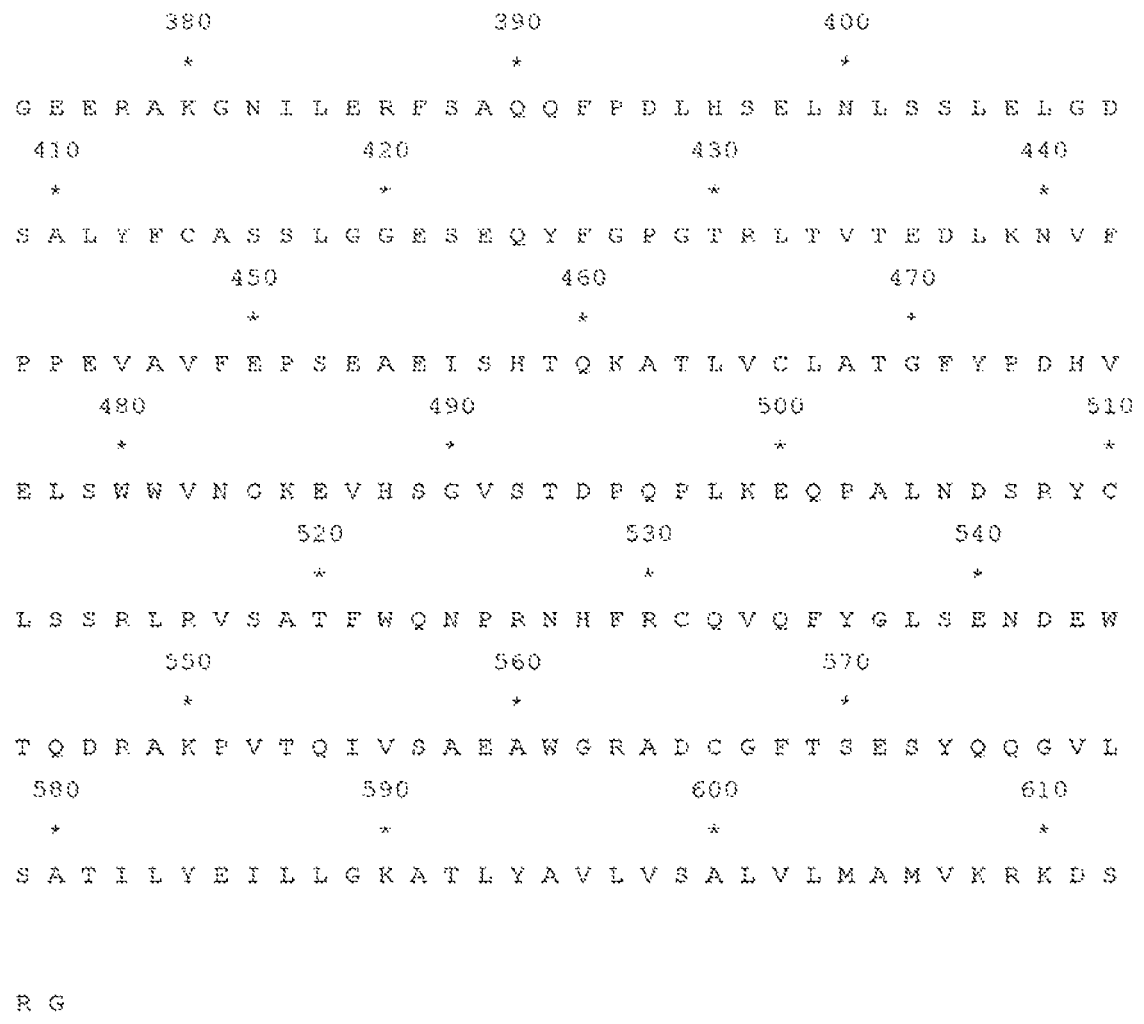

FIG. 8 is the amino acid sequence (SEQ ID No: 24) corresponding to FIG. 7

In FIG. 8:
M1-Q22 is a leader sequence which is removed on maturation of the parental alpha chain TCR;
Q23-S274 corresponds to the parental alpha chain sequence;
Q23-N246 corresponds to the parental alpha chain extracellular domain;
L247-T268 is the alpha chain transmembrane region of the mature TCR;
L269-S274 is the alpha chain intracellular region of the mature TCR;
R277-R280 is the furin cleavage site to assist proteolytic removal, in the Golgi apparatus, of the P2A sequence A285-P303;
G275, S276, S281 to G284, are flexible linkers allowing full function of the furin cleavage and P2A sequences;
R304-V323 is a leader sequence which is removed on maturation of the parental beta chain TCR;
D324-G614 corresponds to the parental beta chain sequence;
D324-E585 corresponds to the parental beta chain extracellular domain;
I586-V607 is the beta chain transmembrane region of the mature TCR;
K608-G614 is the beta chain intracellular region of the mature TCR.

(d) T-Cells Transfected with Parental and High Affinity AFP TCRs

Following the procedures described in (a) and (b) above, the parental AFP alpha-2A-beta TCR gene (SEQ ID No: 23 (FIG. 7)) was inserted into the pELNSxv lenti vector using the NheI and SalI restriction sites unique to both DNA constructs, and transfected T-cells created.

Similarly, T-cells may be created by transfection with genes identical to SEQ ID No: 23 (FIG. 7) except that they encode an alpha chain variable domain having one of SEQ ID Nos: 6 to 20 associated with the variable domain sequence (D1 to T112) of the parental beta chain SEQ ID No: 3;

Example 6

Activation of AFP TCR Engineered T Cells

The following assay was carried out to demonstrate the activation of TCR-transduced cytotoxic T lymphocytes (CTLs) in response to tumour cell lines. IFN-γ production, as measured using the ELISPOT assay, was used as a read-out for cytotoxic T lymphocyte (CTL) activation.

ELISPOTs
Reagents
Assay media: 10% FCS (Gibco, Cat#2011-09), 88% RPMI 1640 (Gibco, Cat#42401), 1% glutamine (Gibco Cat#25030) and 1% penicillin/streptomycin (Gibco Cat#15070-063).
Wash buffer: 0.01M PBS/0.05% Tween 20
PBS (Gibco Cat#10010)
The Human IFNγ ELISPOT kit (BD Bioscience; Cat#551849) containing capture and detection antibodies and Human IFN-γ PVDF ELISPOT 96 well plates, with associated AEC substrate set (BD Bioscience, Cat#551951)
Methods
Target Cell Preparation The target cells used in this method were natural epitope-presenting cells: HepG2 hepatocellular carcinoma cells which are both HLA-A2$^+$ AFP$^+$. HEP2 normal human hepatocytes, which are HLA-A2$^+$ AFP$^-$, were used as a negative control. Sufficient target cells (50,000 cells/well) were washed by centrifugation three times at 1200 rpm, 10 min in a Megafuge® 1.0 (Heraeus). Cells were then re-suspended in assay media at $10^6$ cells/ml.

Effector Cell Preparation

The effector cells (T cells) used in this method were peripheral blood lymphocytes (PBL), obtained by negative selection using CD14 and CD25 microbead kits (Miltenyi Biotech Cat#130-050-201 and 130-092-983 respectively) from freshly isolated peripheral blood mononuclear cells (PBMC) from the venous blood of healthy volunteers. Cells were stimulated with antiCD3/CD28 coated beads (Dynabeads® T cell expander, Invitrogen), transduced with lentivirus carrying the gene encoding the full αβ TCR of interest (based on the construct described in Example 5 and shown in FIG. 7) and expanded in assay media containing 50U/ml IL-2 until between 10 and 13 days post transduction. These cells were then placed in assay media prior to washing by centrifugation at 1200 rpm, 10 min in a Megafuge® 1.0 (Heraeus). Cells were then re-suspended in assay media at a 4× the final required concentration.

Plates were prepared as follows: 100 μl anti-IFN-γ capture antibody was diluted in 10 ml sterile PBS per plate. 100 μl of the diluted capture antibody was then dispensed into each well. The plates were then incubated overnight at 4° C. Following incubation the plates were washed (programme 1, plate type 2, Ultrawash Plus 96-well plate washer; Dynex) to remove the capture antibody. Plates were then blocked by adding 200 μl of assay media to each well and incubated at room temperature for two hours. The assay media was then washed from the plates (programme 1, plate type 2, Ultrawash Plus 96-well plate washer, Dynex) and any remaining media was removed by flicking and tapping the ELISPOT plates on a paper towel.

The constituents of the assay were then added to the ELISPOT plate in the following order:

50 μl of target cells $10^6$ cells/ml (giving a total of 50,000 target cells/well)

50 μl media (assay media)

50 μl effector cells (20,000 TCR-transduced PBL cells/well)

The plates were then incubated overnight (37° C./5% CO2). The next day the plates were washed three times (programme 1, plate type 2, Ultrawash Plus 96-well plate washer, Dynex) with wash buffer and tapped dry on paper towel to remove excess wash buffer. 100 μl of primary detection antibody was then added to each well. The primary detection antibody was diluted into 10 ml of dilution buffer (the volume required for a single plate) using the dilution specified in the manufacturer's instructions. Plates were then incubated at room temperature for at least 2 hours prior to being washed three times (programme 1, plate type 2, Ultrawash Plus 96-well plate washer, Dynex) with wash buffer; excess wash buffer was removed by tapping the plate on a paper towel.

Secondary detection was performed by adding 100 μl of diluted streptavidin-HRP to each well and incubating the plate at room temperature for 1 hour. The streptavidin-HRP was diluted into 10 ml dilution buffer (the volume required for a single plate), using the dilution specified in the manufacturer's instructions. The plates were then washed three times (programme 1, plate type 2, Ultrawash Plus 96-well plate washer, Dynex) with wash buffer and tapped on paper towel to remove excess wash buffer. Plates were then washed twice with PBS by adding 200 μl to each well, flicking the buffer off and tapping on a paper towel to remove excess buffer. No more than 15 mins prior to use, one drop (20 μl) of AEC chromogen was added to each 1 ml of AEC substrate and mixed. 10 ml of this solution was prepared for each plate; 100 μl was added per well. The plate was then protected from light using foil, and spot development monitored regularly, usually occurring within 5-20 mins. The plates were washed in tap water to terminate the development reaction, and shaken dry prior to their disassembly into three constituent parts. The plates were then allowed to dry at room temperature for at least 2 hours prior to counting the spots using an Immunospot® Plate reader (CTL; Cellular Technology Limited).

Results

IFNγ release by activated TCR-transduced T cells in response to a variety of AFP-positive and control tumour cell lines was tested by ELISPOT assay (as described above). The number of ELISPOT spots observed in each well was plotted using Graph Pad Prism®.

CD4+, CD8+ or mixed CD4+/CD8+ T cells expressing the WT TCR or one of TCR Nos:1-5 (as described in the table below) were incubated with AFP+ HLA:A2+ tumour cell line HepG2 or with AFP-HLA:A2+ HEP2 normal hepatocytes. A sample containing no T cells was used as a control.

| TCR No | TCR α variable domain SEQ ID NO: | TCR β variable domain SEQ ID NO: |
|---|---|---|
| 1 | 11 | D1 to T112 of SEQ ID No: 3 |
| 2 | 12 | D1 to T112 of SEQ ID No: 3 |
| 3 | 13 | D1 to T112 of SEQ ID No: 3 |
| 4 | 14 | D1 to T112 of SEQ ID No: 3 |
| 5 | 15 | D1 to T112 of SEQ ID No: 3 |

FIG. 9 demonstrates that T cells transduced with the TCRs described in the table above are activated in response to AFP positive tumour cells (HepG2). Activation of these variant TCRs is greater than for the WT TCR. Activation by AFP negative normal hepatocytes (HEP2) is minimal demonstrating the specificity of the TCRs for AFP.

The invention is further described by the following numbered paragraphs:

1. A non-naturally occurring and/or purified and/or engineered T cell receptor (TCR) having the property of binding to FMNKFIYEI (SEQ ID No: 1) HLA-A2 complex and comprising at least one TCR alpha chain variable domain and/or at least one TCR beta chain variable domain,
    the alpha chain variable domain comprising an amino acid sequence that has at least 90% identity to the sequence of amino acid residues 1-112 of SEQ ID No: 2, and/or
    the beta chain variable domain comprising an amino acid sequence that has at least 90% identity to the sequence of amino acid residues 1-112 of SEQ ID No: 3.

2. The TCR of paragraph 1, wherein the alpha chain variable domain includes a mutation in one or more of the amino acids corresponding to 31Q, 32S, 94D, 95S, 96G, 97Y and 98A.

3. The TCR of paragraph 1 or paragraph 2, wherein the alpha chain variable domain includes at least one of the following mutations:

| Residue no. | | |
|---|---|---|
| 31Q | F | Y |
| 32S | A | |
| 94D | Q | |
| 95S | N | |
| 96G | S | |
| 97Y | V | |
| 98A | S | |

4. The TCR of any preceding paragraph, wherein the alpha chain variable domain comprises an amino acid sequence having at least 90% identity to residues 1-112 of any one of SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, SEQ ID No: 16, SEQ ID No: 17, SEQ ID No: 18, SEQ ID No: 19 and SEQ ID No: 20.

5. The TCR of any preceding paragraph, wherein the alpha chain variable domain comprises Q1 to H112 of SEQ ID No: 11, SEQ ID No 12 or SEQ ID No 13 and/or the beta chain variable domain comprise D1 to T112 of SEQ ID No: 3.

6. The TCR of paragraph 1, wherein the alpha chain variable domain comprises amino acid resides 1-112 of SEQ ID No: 2, and the beta chain variable domain comprises amino acid residues 1-112 of SEQ ID No: 3.

7. The TCR of any preceding paragraph having an alpha chain TRAC constant domain sequence and/or a beta chain TRBC1 or TRBC2 constant domain sequence.

8. The TCR of paragraph 7, wherein, the alpha and/or beta chain constant domain sequence(s) are modified by truncation or substitution to delete the native disulfide bond between Cys4 of exon 2 of TRAC and Cys2 of exon 2 of TRBC1 or TRBC2.

9. The TCR of paragraph 7 or paragraph 8, wherein the alpha and/or beta chain constant domain sequence(s) are modified by substitution of cysteine residues for Thr 48 of TRAC and Ser 57 of TRBC1 or TRBC2, the cysteines forming a disulfide bond between the alpha and beta constant domains of the TCR.

10. The TCR of any preceding paragraph, which is in single chain format of the type Vα-L-Vβ, Vβ-L-Vα, Vα-Cα-L-Vβ, Vα-L-Vβ-Cβ or Vα-Cα-L-Vβ-Cβ wherein Vα and Vβ are TCR α and β variable regions respectively, Cα and Cβ are TCR α and β constant regions respectively, and L is a linker sequence.

11. The TCR of any one of paragraphs 1-9, which is an alpha-beta heterodimer.

12. The TCR of any preceding paragraph associated with a detectable label, a therapeutic agent or a PK modifying moiety.

13. Non-naturally occurring and/or purified and/or engineered nucleic acid encoding the TCR of any one of the preceding paragraphs.

14. A non-naturally occurring and/or purified and/or engineered cell, especially a T-cell, presenting a TCR of any one of paragraphs 1-12.

15. A cell harbouring
(a) a TCR expression vector which comprises nucleic acid of paragraph 13 encoding in a single open reading frame, or two distinct open reading frames, the alpha chain and the beta chain respectively; or
(b) a first expression vector which comprises nucleic acid encoding the alpha chain of a TCR of any of paragraphs 1 to 12, and a second expression vector which comprises nucleic acid encoding the beta chain of a TCR of any of paragraphs 1 to 12.

16. A pharmaceutical composition comprising a TCR of any one of paragraphs 1 to 12 or a cell of paragraph 14 or paragraph 15, together with one or more pharmaceutically acceptable carriers or excipients.

17. A non-naturally occurring and/or purified and/or engineered TCR which binds the FMNKFIYEI (SEQ ID No: 1) peptide presented as a peptide-HLA-A2 complex, or a cell expressing and/or presenting such a TCR, for use in medicine.

18. The TCR or cell for use of paragraph 17, for use in a method of treating cancer.

19. The TCR or cell for use of paragraph 18, wherein the method comprises adoptive therapy.

20. The TCR or cell for use of any one of paragraphs 17 to 19, wherein the TCR is in any one of paragraphs 1 to 12 and/or wherein the cell is of paragraph 14 or paragraph 15.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. "A method for treating a patient expressing a FMNK-FIYEI (SEQ ID NO: 1)-HLA-A2 complex comprising: (a) administering to the patient an immune cell comprising a non-naturally occurring and/or purified and/or engineered T cell receptor (TCR) having the property of binding to said FMNKFIYEI (SEQ ID NO: 1) HLA-A2 complex or (b) administering to the patient a non-naturally occurring and/or purified and/or engineered T cell receptor (TCR) having the property of binding to said FMNKFIYEI (SEQ ID NO: 1) HLA-A2 complex wherein said TCR further comprises a therapeutic agent, wherein the TCR of (a) or (b) comprises at least one TCR alpha chain variable domain and at least one TCR beta chain variable domain, wherein the alpha chain variable domain comprises at least one of the following sets of CDR sequences:"

| CDR1 | DRGSQA | residues 27 to 32 of SEQ ID NO: 6 |
| CDR2 | IYSNGD | residues 50 to 55 of SEQ ID NO: 6 |
| CDR3 | AVNSDS GYALNF | residues 90 to 101 of SEQ ID NO: 6 | or

| CDR1 | DRGSQS | residues 27 to 32 of SEQ ID NO: 7 |
| CDR2 | IYSNGD | residues 50 to 55 of SEQ ID NO: 7 |
| CDR3 | AVNSDS SYALNF | residues 90 to 101 of SEQ ID NO: 7 | or

| CDR1 | DRGSQS | residues 27 to 32 of SEQ ID NO: 8 |
| CDR2 | IYSNGD | residues 50 to 55 of SEQ ID NO: 8 |
| CDR3 | AVNSDS GVALNF | residues 90 to 101 of SEQ ID NO: 8 | or

```
CDR1    DRGSQA    residues 27 to 32 of SEQ ID NO: 9
CDR2    IYSNGD    residues 50 to 55 of SEQ ID NO: 9
CDR3    AVNSDS    residues 90 to 101 of SEQ ID NO: 9
        GVALNF
or CDR1    DRGSQS    residues 27 to 32 of SEQ ID NO: 10
CDR2    IYSNGD    residues 50 to 55 of SEQ ID NO: 10
CDR3    AVNSQS    residues 90 to 101 of SEQ ID NO: 10
        GYALNF
or CDR1    DRGSQS    residues 27 to 32 of SEQ ID NO: 11
CDR2    IYSNGD    residues 50 to 55 of SEQ ID NO: 11
CDR3    AVNSQS    residues 90 to 101 of SEQ ID NO: 11
        GYSLNF
or CDR1    DRGSQS    residues 27 to 32 of SEQ ID NO: 12
CDR2    IYSNGD    residues 50 to 55 of SEQ ID NO: 12
CDR3    AVNSQS    residues 90 to 101 of SEQ ID NO: 12
        SYALNF
or CDR1    DRGSQA    residues 27 to 32 of SEQ ID NO: 13
CDR2    IYSNGD    residues 50 to 55 of SEQ ID NO: 13
CDR3    AVNSQS    residues 90 to 101 of SEQ ID NO: 13
        GYALNF
or CDR1    DRGSQS    residues 27 to 32 of SEQ ID NO: 14
CDR2    IYSNGD    residues 50 to 55 of SEQ ID NO: 14
CDR3    AVNSQS    residues 90 to 101 of SEQ ID NO: 14
        GVALNF
or CDR1    DRGSQS    residues 27 to 32 of SEQ ID NO: 15
CDR2    IYSNGD    residues 50 to 55 of SEQ ID NO: 15
CDR3    AVNSQN    residues 90 to 101 of SEQ ID NO: 15
        GYALNF
or CDR1    DRGSFS    residues 27 to 32 of SEQ ID NO: 16
CDR2    IYSNGD    residues 50 to 55 of SEQ ID NO: 16
CDR3    AVNSDS    residues 90 to 101 of SEQ ID NO: 16
        GYALNF
or CDR1    DRGSYS    residues 27 to 32 of SEQ ID NO: 17
CDR2    IYSNGD    residues 50 to 55 of SEQ ID NO: 17
CDR3    AVNSDS    residues 90 to 101 of SEQ ID NO: 17
        GYALNF
or CDR1    DRGSYS    residues 27 to 32 of SEQ ID NO: 18
CDR2    IYSNGD    residues 50 to 55 of SEQ ID NO: 18
CDR3    AVNSDS    residues 90 to 101 of SEQ ID NO: 18
        SYALNF
or CDR1    DRGSYS    residues 27 to 32 of SEQ ID NO: 19
CDR2    IYSNGD    residues 50 to 55 of SEQ ID NO: 19
CDR3    AVNSDS    residues 90 to 101 of SEQ ID NO: 19
        GVALNF
or CDR1    DRGSYS    residues 27 to 32 of SEQ ID NO: 20
CDR2    IYSNGD    residues 50 to 55 of SEQ ID NO: 20
CDR3    AVNSQS    residues 90 to 101 of SEQ ID NO: 20
        GYALNF
``` and the wherein the beta chain variable domain comprises the following set of CDR sequences:

```
CDR1    SGDLS     residues 27 to 31 of SEQ ID NO: 5
CDR2    YYNGEE    residues 49 to 54 of SEQ ID NO: 5
CDR3    ASSLGG    residues 92 to 102 of SEQ ID NO: 5
        ESEQF
``` wherein the TCR further comprises a therapeutic agent or is expressed in an immune cell.

2. The method of claim 1 wherein the treating is treating cancer.

3. The method of claim 2 wherein the treating cancer is treating hepatocellular carcinoma.

4. The method of claim 1 wherein the treating comprises treating hepatocellular carcinoma.

5. The method of claim 1 wherein the treating comprises adoptive therapy.

6. The method of claim 1, wherein the treating comprises treating alpha Fetoprotein (AFP) positive tumor cells.

* * * * *

UNITED STATES PATENT AND TRADEMARK OFFICE
CERTIFICATE OF CORRECTION

PATENT NO. : 11,084,862 B2
APPLICATION NO. : 16/416907
DATED : August 10, 2021
INVENTOR(S) : Peter Molloy et al.

It is certified that error appears in the above-identified patent and that said Letters Patent is hereby corrected as shown below:

On the Title Page

The Abstract should read as follows:
(57) ABSTRACT
The present invention relates to T cell receptors (TCRs) which bind the HLA-A2 restricted FMNKFIYEI (158-166) peptide (SEQ ID NO: 1) epitope derived from α Fetoprotein (AFP). Certain preferred TCRs of the invention demonstrate excellent binding characteristics and specificity profiles for this AFP epitope. T cell receptors of the invention may comprise at least one TCR alpha chain variable domain and/or at least one TCR beta chain variable domain, the alpha chain variable domain which may comprise an amino acid sequence that has at least 90% identity to the sequence of amino acid residues 1-112 of (SEQ ID NO: 2), and/or the beta chain variable domain which may comprise an amino acid sequence that has at least 90% identity to the sequence of amino acid residues 1-112 of (SEQ ID NO: 3).

In the Specification

Column 1, beginning at Line 32, should read as follows:
The instant application contains a Sequence Listing which has been submitted electronically in ASCII format and is hereby incorporated by reference in its entirety. Said ASCII copy, created on June 22, 2021, is named Y7975-01005_SL.txt and is 49,502 bytes in size.

Column 1, beginning at Line 40, should read as:
The present invention relates to T cell receptors (TCRs) which bind the HLA-A2 restricted FMNKFIYEI (158-166) (SEQ ID NO: 1) peptide epitope derived from α Fetoprotein (AFP). Certain preferred TCRs of the invention demonstrate excellent binding characteristics and specificity profiles for this AFP epitope.

Column 7, beginning at Line 29, should read as:
The TCRs of the invention have the property of binding the FMNKFIYEI (SEQ ID No: 1) HLA-A2 complex. Certain TCRs of the invention have been found to be highly suitable for use in adoptive Signed and Sealed this
First Day of October, 2024

*Katherine Kelly Vidal*

Katherine Kelly Vidal
*Director of the United States Patent and Trademark Office*

CERTIFICATE OF CORRECTION (continued)
U.S. Pat. No. 11,084,862 B2 therapy. Such TCRs may have a KD for the complex of less than the parental AFP TCR, for example from about 1 μM to about 21 μM and/or have a binding half-life (T½) for the complex in the range of from less than 0.5 seconds to about 2 seconds. Increasing the binding affinity of a native TCR often reduces the selectivity of the TCR for its peptide-MHC ligand, and this is demonstrated in Zhao Yangbing et al., (J. Immunol, 2007 179: 9, p5845-5854). However, certain TCRs of the invention remain selective for the FMNKFIYEI (SEQ ID NO: 1) HLA-A2 complex, despite, in some embodiments, having higher binding affinity than the parental AFP TCR (see Example 6).

Column 10, beginning at Lines 22, 29, 33 and 38 respectively should read as:
Also provided by the invention are:
a non-naturally occurring and/or purified and/or engineered TCR which binds the FMNKFIYEI peptide (SEQ ID NO: 1) presented as a peptide-HLA-A2 complex, or a cell expressing and/or presenting such a TCR, for use in medicine, preferably in a method of treating cancer. The method may comprise adoptive therapy;
the use of a TCR which binds the FMNKFIYEI peptide (SEQ ID NO: 1) presented as a peptide-HLA-A2 complex, or a cell expressing and/or presenting such a TCR, in the manufacture of a medicament for treating cancer;
a method of treating cancer in a patient, which may comprise administering to the patient a TCR which binds the FMNKFIYEI peptide (SEQ ID NO: 1) presented as a peptide-HLA-A2 complex, or a cell expressing and/or presenting such a TCR.
It is preferred that the TCR which binds the FMNKFIYEI peptide (SEQ ID NO: 1) presented as a peptide-HLA-A2 complex is a TCR of the invention.

Column 14, beginning at Line 23 should read as:
TCR was injected over two different cells one coated with ~1000 RU of FMNKFIYEI (SEQ ID NO: 1) HLA-A*02 complex, the second coated with ~1000 RU of non-specific HLA-A2-peptide complex. Flow rate was set at 50 μl/min. Typically 250 μl of TCR at ~ 1 μM concentration was injected. Buffer was then flowed over until the response had returned to baseline or >2 hours had elapsed. Kinetic parameters were calculated using BIAevaluation® software. The dissociation phase was fitted to a single exponential decay equation enabling calculation of half-life.

In the Claims

Claim 1, Column 53, beginning at Line 51:
Remove the """" at the beginning of the claim and at Line 67, at the end of the paragraph Claim 1, Column 56, beginning at Line 23, should read as:
and wherein the beta chain variable domain comprises the following set of CDR sequences:
| | | |
|---|---|---|
| CDR1 | SGDLS | residues 27 to 31 of SEQ ID NO: 5 |
| CDR2 | YYNGEE | residues 49 to 54 of SEQ ID NO: 5 |
| CDR3 | ASSLGGESEQY | residues 92 to 102 of SEQ ID NO: 5 |

Claim 1, Column 56, beginning at Line 33 to Line 34 is deleted